US008636738B2

(12) United States Patent
McClintock et al.

(10) Patent No.: US 8,636,738 B2
(45) Date of Patent: Jan. 28, 2014

(54) DYNAMIC CERVICAL PLATE

(75) Inventors: Larry McClintock, Gore, VA (US); Todd Wallenstein, Ashburn, VA (US); Peter Harris, Leesburg, VA (US); Kevin R. Strauss, Leesburg, VA (US); Megan Carnes, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 119 days.

(21) Appl. No.: 12/766,438

(22) Filed: Apr. 23, 2010

(65) Prior Publication Data

US 2010/0234888 A1  Sep. 16, 2010

Related U.S. Application Data

(63) Continuation-in-part of application No. PCT/US2008/080897, filed on Oct. 23, 2008.

(60) Provisional application No. 61/000,070, filed on Oct. 23, 2007, provisional application No. 61/280,796, filed on Nov. 9, 2009.

(51) Int. Cl.
   *A61B 17/56* (2006.01)
   *A61B 17/58* (2006.01)
   *A61B 17/80* (2006.01)
   *A61F 2/30* (2006.01)

(52) U.S. Cl.
   USPC ............................... 606/71; 606/280; 606/70

(58) Field of Classification Search
   USPC ....................... 606/280–299, 70, 71
   See application file for complete search history.

(56) References Cited

U.S. PATENT DOCUMENTS

| 3,426,364 | A | 2/1969 | Lumb |
| 5,484,439 | A | 1/1996 | Olson et al. |
| 5,616,142 | A | 4/1997 | Yuan et al. |
| 5,681,312 | A | 10/1997 | Yuan et al. |
| 5,713,900 | A | 2/1998 | Benzel et al. |
| 5,843,082 | A | 12/1998 | Yuan et al. |

(Continued)

FOREIGN PATENT DOCUMENTS

WO   WO 2005/062900 A2   7/2005

OTHER PUBLICATIONS

International Search Report corresponding to Intternational Application No. PCT/US2008/080897; date of completion of the search: Dec. 15, 2008; date of mailing of the search: Jan. 8, 2009; 2 pages.

*Primary Examiner* — Kevin T Truong
*Assistant Examiner* — Si Ming Lee
(74) *Attorney, Agent, or Firm* — Carter, DeLuca, Farrell & Schmidt, LLP

(57) ABSTRACT

A dynamic cervical plate includes a first end section and a second end section. In embodiments, the dynamic cervical plate may include one or more middle sections positioned between the first and second end sections. Each section may be longitudinally repositionable. Each section may include a plurality of openings for receiving threaded fasteners such as a self-starting screw or a self-tapping screw. In addition, each section may include an orifice for releasably mating with a drill guide. Each of the end sections may include a notch at one end for aligning with the drill guide or fixation pins. In one embodiment, a pin is used to interconnect the sections. In other embodiments, support bars are used to limit flexure between sections. In embodiments, one or more locking elements and/or one or more support bars may operably interconnect each section.

18 Claims, 17 Drawing Sheets

(56) References Cited

U.S. PATENT DOCUMENTS

| | | |
|---|---|---|
| 6,402,756 B1 | 6/2002 | Ralph et al. |
| 6,503,250 B2 | 1/2003 | Paul |
| 6,623,486 B1 * | 9/2003 | Weaver et al. ............... 606/281 |
| 7,186,254 B2 | 3/2007 | Dinh et al. |
| 7,186,256 B2 | 3/2007 | Michelson |
| 7,273,481 B2 | 9/2007 | Lombardo et al. |
| 7,291,152 B2 | 11/2007 | Abdou |
| 7,303,564 B2 | 12/2007 | Freid et al. |
| 7,306,605 B2 | 12/2007 | Ross |
| 7,318,825 B2 | 1/2008 | Butler et al. |
| 7,331,961 B2 | 2/2008 | Abdou |
| 7,341,590 B2 | 3/2008 | Ferree |
| 7,344,537 B1 | 3/2008 | Mueller |
| 7,479,143 B2 | 1/2009 | Suh et al. |
| 7,621,914 B2 | 11/2009 | Ralph et al. |
| 2002/0052605 A1 * | 5/2002 | Grooms et al. ............... 606/72 |
| 2004/0015172 A1 * | 1/2004 | Biedermann et al. ............ 606/73 |
| 2005/0043732 A1 * | 2/2005 | Dalton ............ 606/61 |
| 2005/0137597 A1 * | 6/2005 | Butler et al. ............ 606/69 |
| 2006/0009845 A1 | 1/2006 | Chin |
| 2006/0200134 A1 * | 9/2006 | Freid et al. ............ 606/61 |
| 2006/0235405 A1 * | 10/2006 | Hawkes ............ 606/69 |
| 2007/0233117 A1 | 10/2007 | Butler et al. |
| 2008/0108998 A1 | 5/2008 | Lindemann |
| 2008/0154312 A1 | 6/2008 | Colleran et al. |
| 2008/0161854 A1 | 7/2008 | Bae et al. |
| 2008/0234680 A1 * | 9/2008 | Zaiser et al. ............ 606/71 |
| 2008/0234681 A1 | 9/2008 | Baynham |
| 2008/0269753 A1 | 10/2008 | Cannestra |
| 2009/0043341 A1 | 2/2009 | Tyber et al. |
| 2009/0076509 A1 | 3/2009 | Bush, Jr. et al. |

\* cited by examiner

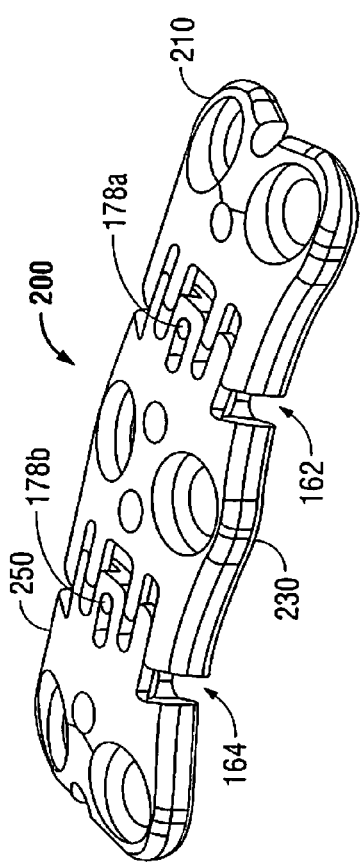
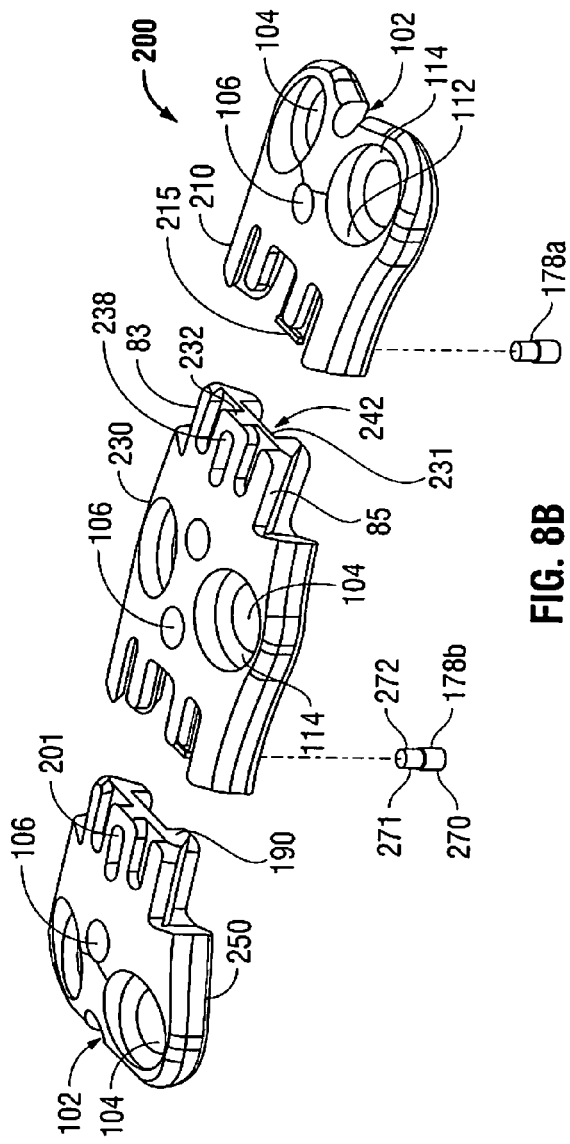
FIG. 8A
FIG. 8B

DYNAMIC CERVICAL PLATE

CROSS-REFERENCE TO RELATED APPLICATIONS

This application is a continuation-in-part of International Application No. PCT/US08/80897, filed on Oct. 23, 2008, which claims the benefit of and priority to U.S. Provisional Patent Application Ser. No. 61/000,070, filed Oct. 23, 2007, and U.S. Provisional Patent Application Ser. No. 61/280,796, filed on Nov. 9, 2009, the entire contents of each of the prior applications are incorporated by reference herein.

BACKGROUND

1. Technical Field

The present disclosure relates generally to a spinal plate and, more particularly, to a dynamic cervical plate.

2. Background of Related Art

The human spinal column is a highly complex structure. It includes more than twenty discrete bones, known as vertebrae, coupled sequentially to one another to house and protect critical elements of the nervous system. The cervical portion of the spine, which comprises the top of the spine up to the base of the skull, includes the first seven vertebrae.

For many reasons, such as aging and trauma, the intervertebral discs can begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. However, should the prosthetic protrude from between the adjacent vertebrae and thereby contact the surrounding nerves or tissues, the patient may experience additional discomfort. In procedures for remedying this problem, a spinal plate is affixed to the vertebrae and oriented to minimize such protrusion.

Spinal plates, and cervical plates in particular, are known in the art. Fixed cervical plates generally exhibit unalterable, static dimensions. During the natural subsidence of the spinal column over time, its overall length gradually decreases. Fixed cervical plates resist this change due to their fixed axial length, which may eventually stress the spine and cause pain or discomfort. Adjustable cervical plates attend to this predicament by providing a mechanism through which the plate is shortened to accommodate for a measure of subsidence. However, the known adjustable plates require subsequent surgical procedures to adjust the axial dimension of the plate.

SUMMARY

The present disclosure relates to a spinal plate apparatus including a first section having a tongue and a pair of fingers extending along a longitudinal axis from one end thereof. The pair of fingers defines grooves along an interior surface. A second section has bars for slidably engaging the grooves and spaces for receiving the tongue and fingers. Each section moves relative to one another accommodating subsidence of selected vertebral bodies and limiting longitudinal expansion without additional invasive procedures.

One embodiment includes a third section having second bars and one or more spaces for receiving a second tongue and a second pair of fingers disposed on the opposing distal end of the second section. The second pair of fingers defines second grooves along an interior surface. The second bars slidably engage the second grooves so that the second and third sections are slidably engaged along the longitudinal axis.

In other embodiments, one or more support bars are slidably disposed between two or more of the sections. Each support bar may be slidably disposed in one or more support bar cavities. The support bar cavities are longitudinally disposed within the sections.

In another embodiment, one or more pins interconnect two or more sections. One pin connection may be disposed between the first and second sections and a second pin connection may be disposed between second and third sections. Furthermore, each pin may be at least partially disposed in a pin hole of one section and at least partially disposed in a slide cavity of another section. As such, the one or more pins and the one or more slide cavities are configured and dimensioned to provide a minimum and a maximum longitudinal gap distance between each section.

One or more sections include one or more openings having an annular lip configured and dimensioned to receive a fastener. Furthermore, one or more of the sections may include one or more orifices and/or a notch that is configured and dimensioned to receive a drill guide. In some manifestations, one or more sections include one or more teeth disposed on the tongue of one section configured and dimensioned to engage either one or more ridges disposed on the underside of the perimeter of the slide cavity or a lip disposed on the proximal end of another section.

In one aspect, a spinal plate system includes two or more sections, one or more support bars, and at least one locking element. The two or more sections are slidably engagable with one another such that each section is movable relative to the other along a longitudinal axis thereof. One or more of the two or more sections are adapted to engage one or more screws for mounting the two or more sections to one or more vertebral bodies. The one or more support bars and the one or more locking elements operably interconnect the two or more sections such that the two or more sections are inhibited from expanding along the longitudinal axis thereof. One or more of the first and second sections may include a relief aperture that permits the infinite adjustment of the one or more first and second sections relative to one another.

The one or more screws are formed of a first material and the two or more sections are formed of a second material. One of the first and second materials is softer than the other such that when the one or more screws are engaged with one or more of the two or more sections, the one or more screws are inhibited from disengaging from the two or more sections.

The one or more locking elements include one or more fins extending therefrom that may be adapted to engage the one or more support bars. The one or more fins define a profile that may be adapted to engage the one or more support bars such that the surface of the profile may contact the support bar. The locking element may include two fins that are disposed longitudinally adjacent relative to a longitudinal axis of the locking element. The locking element may include a first fin that forms an arc relative to a longitudinal axis of the locking element and a second fin that is disposed substantially perpendicular to the longitudinal axis of the locking element.

In embodiments, a third section may be slidably engageable with one or more of the first and second sections. The third section may be operably coupled to the one or more first and second sections with a second support bar and a second locking element.

BRIEF DESCRIPTION OF THE DRAWINGS

The above and other aspects, features, and advantages of the present disclosure will become more apparent in light of the following detailed description when taken in conjunction with the accompanying drawings in which:

FIG. 8A is a perspective view of another embodiment of the dynamic cervical plate in accordance with the present disclosure;

FIG. 8B is an exploded perspective view, with parts separated, of the dynamic cervical plate of FIG. 8A;

DETAILED DESCRIPTION OF THE EMBODIMENTS

Figure 1A:
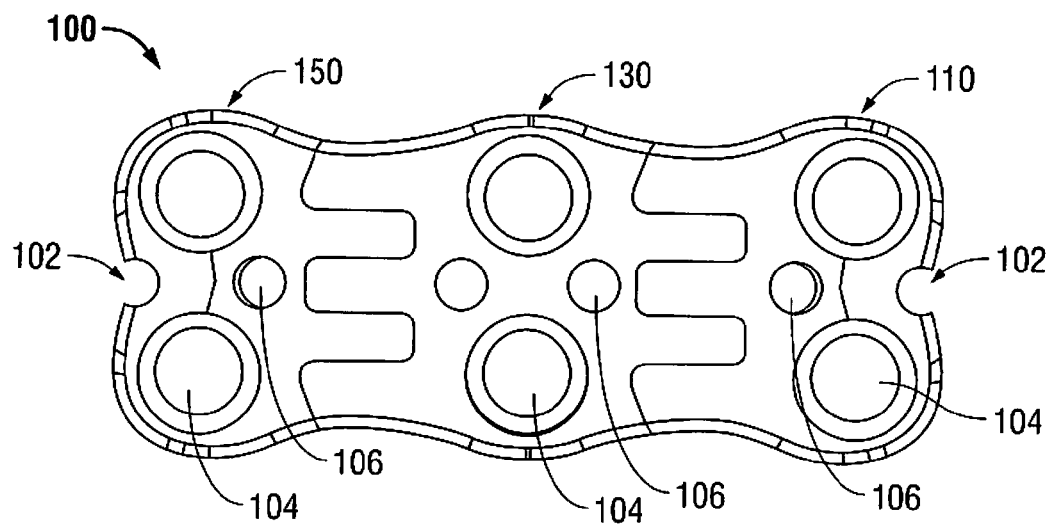
FIG. 1A is a top plan view of the dynamic cervical plate in a first state.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure with unnecessary detail.

Figure 1B:
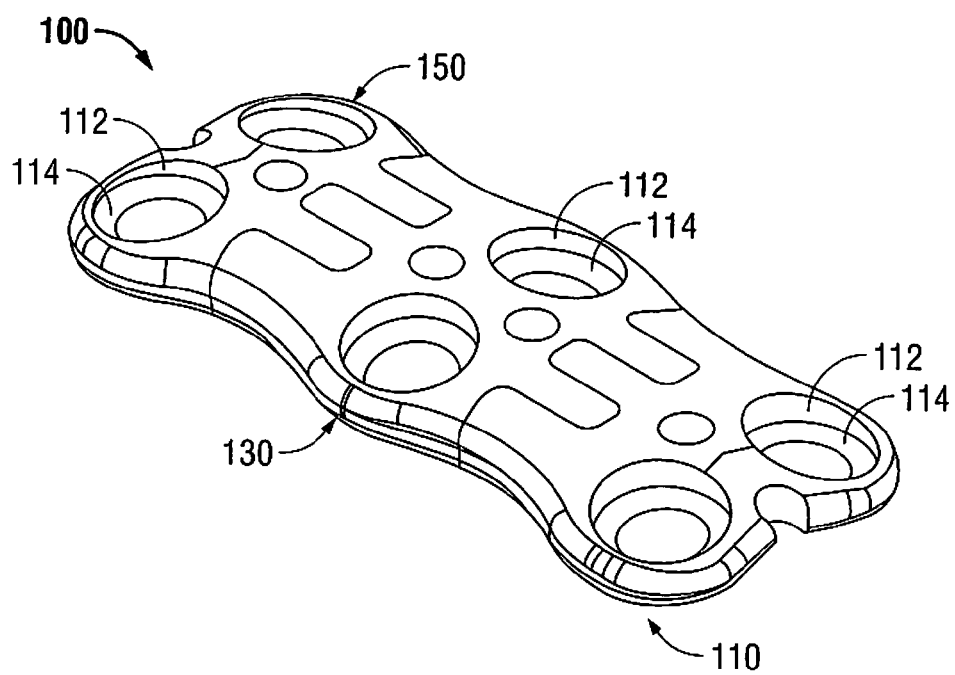
FIG. 1B is a perspective view of the dynamic cervical plate of FIG. 1A.

Referring now to the drawings, in which like reference numerals identify identical or substantially similar parts throughout the several views, FIGS. 1A-1B illustrate a dynamic cervical plate that is generally designated as 100. The dynamic cervical plate 100 includes a first end section 110, a middle section 130, and a second end section 150. As shown in FIGS. 1A and 1B, the dynamic cervical plate 100 is in a collapsed or first state. As such, the end sections 110, 130 are in close proximity to the middle section 150. In the first state, the dynamic cervical plate 100 has a minimum overall length. Each of the sections 110, 130, 150 includes a Plurality of openings 104 and at least one orifice 106. The first end section 110 and the second end section 130 also include a notch 102. The notch 102 and the orifice 106 are also intended to be used for temporary fixation pins as well as plate holders. Each of the openings 104 has an annular sidewall 112 extending downwards from the top surface. A lip 114 is located in each opening 104 in proximity to the bottom surface of the respective section 110, 130, 150. Each of the sections 110, 130, 150 also includes at least one orifice 106 adapted for receiving a post of a drill guide or fixation pins as is known in the art. It is contemplated that a drill guide having such a post or extension includes guide tubes for aligning a drill bit with the target vertebral body. An example of a suitable drill guide is disclosed in U.S. patent application Ser. No. 11/895,216, filed Aug. 23, 2007, the entire contents of which are hereby incorporated by reference.

Figure 2:
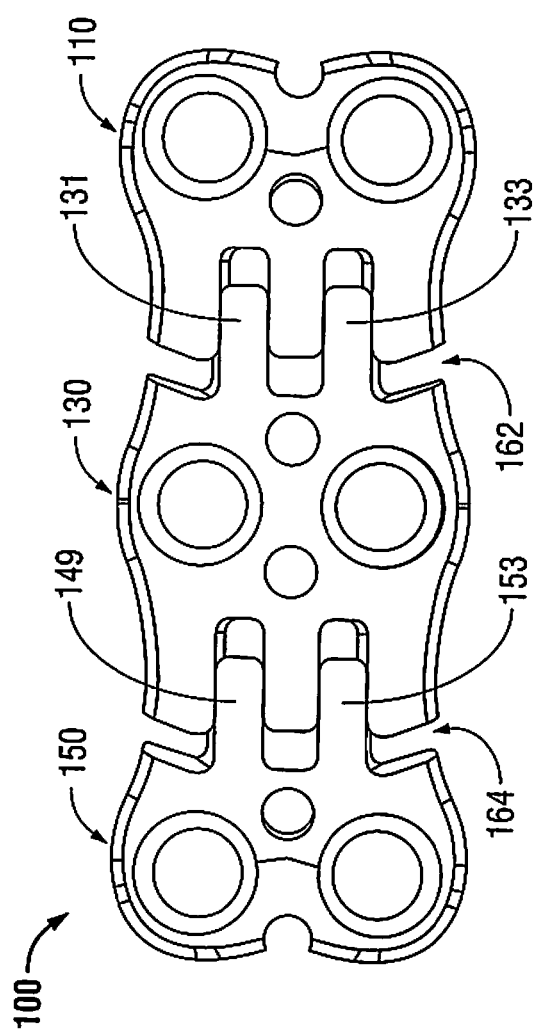
FIG. 2 is a top Plan view of the dynamic cervical plate in a second state.

As shown in FIG. 2, the dynamic cervical plate 100 is in an extended or second state, wherein gaps 162, 164 are defined between the adjacent plate sections 110, 130, 150. The first end section 110 and the second end section 150 are movable along a longitudinal axis towards and away from the middle section 150. By moving the first and second end sections 110, 150 relative to the middle section 130, the gaps 162, 164 are varied and are not necessarily of equal dimensions. Adjustment of the dynamic cervical plate 100 will be discussed in further detail hereinbelow.

Figure 3A:
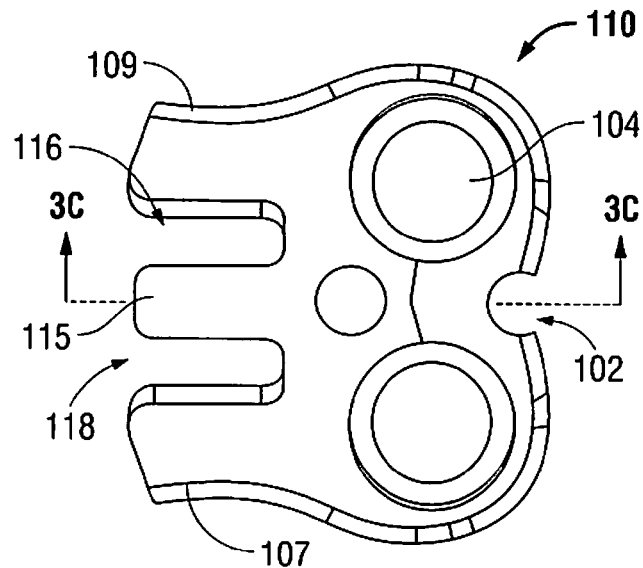
FIG. 3A is a top plan view of a first end section of the dynamic cervical plate of FIG. 1A delineating section line 3C-3C.
Figure 3B:
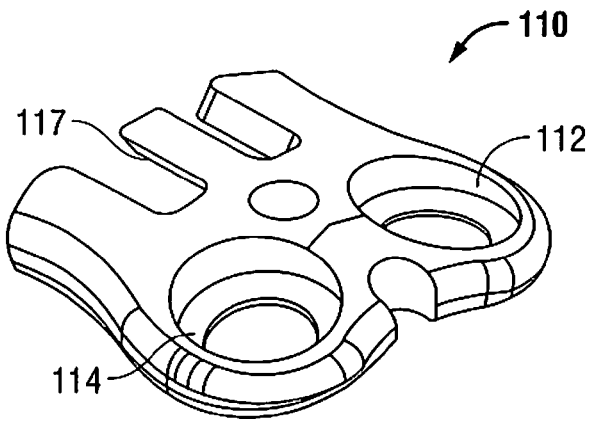
FIG. 3B is a perspective view of the first end section of FIG. 3A.
Figure 3C:
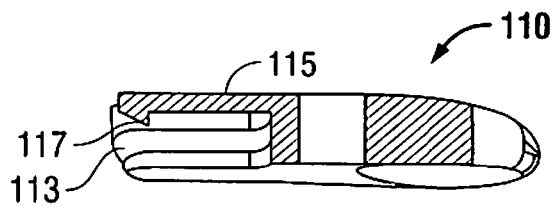
FIG. 3C is a side cross-sectional view of the first end section of FIG. 3A taken along section line 3C-3C.

In FIGS. 3A-3C, details of the first end section 110 are illustrated. The first end section 110 includes a tongue 115 and fingers 107, 109 that extend longitudinally. The tongue 115 and fingers 107, 109 define receiving spaces 116, 118. A tooth 117 extends downwards from the distal end of the tongue 115. A groove 113 is located in the receiving spaces 116, 118. The tongue 115 is flexibly connected to the first end section 110 and is adapted to move above and below the plane defined by the upper surface of the first end section 110. The interaction between the first end section 110 and the middle section 130 will be discussed in further detail hereinbelow.

Figure 4A:
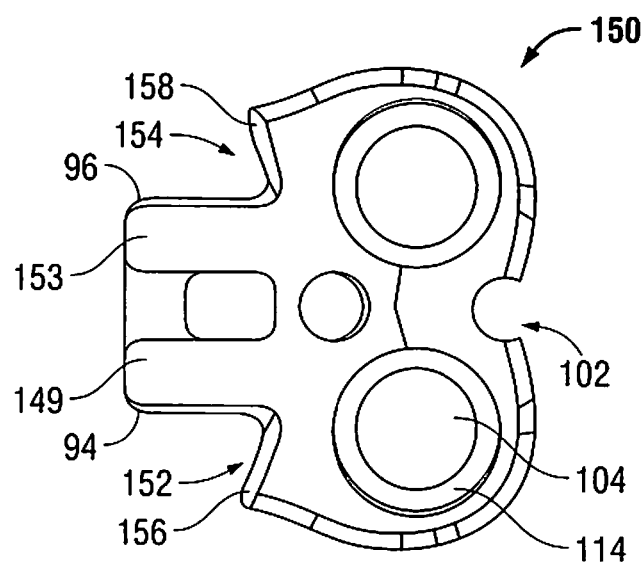
FIG. 4A is a top plan view of a second end section of the dynamic cervical plate of FIG. 1A.
Figure 4B:
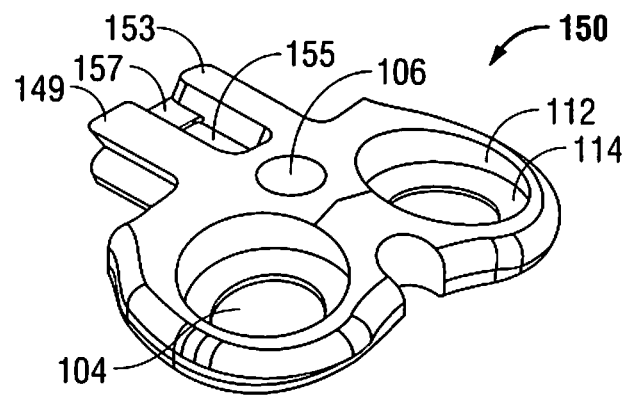
FIG. 4B is a perspective view of the second end section of FIG. 4A.

In FIGS. 4A-4B, details of the second end section 150 are shown. The second end section 150 includes bars 149, 153 that extend along the longitudinal axis of the second end section 150. A lip 157 can extend transversely to the longitudinal axis and can connect the distal ends of the bars 149, 153. A space 155 is defined between the bars 149, 153 and the lip 157. The bars 149, 153 include lateral bars 94, 96. Finger spaces 152, 154 are defined by the exterior side walls of the bars 149, 153, the lateral bars 94, 96, and stop flanges 156, 158. The interaction between the second end section 150 and the middle section 130 will be discussed in further detail hereinbelow.

Figure 5A:
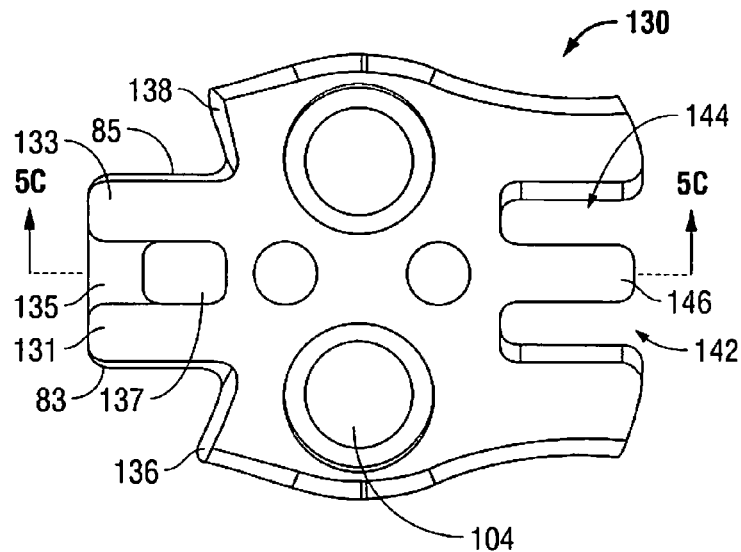
FIG. 5A is a top plan view of a middle section of the dynamic cervical plate of FIG. 1A delineating section line 5C-5C.
Figure 5B:
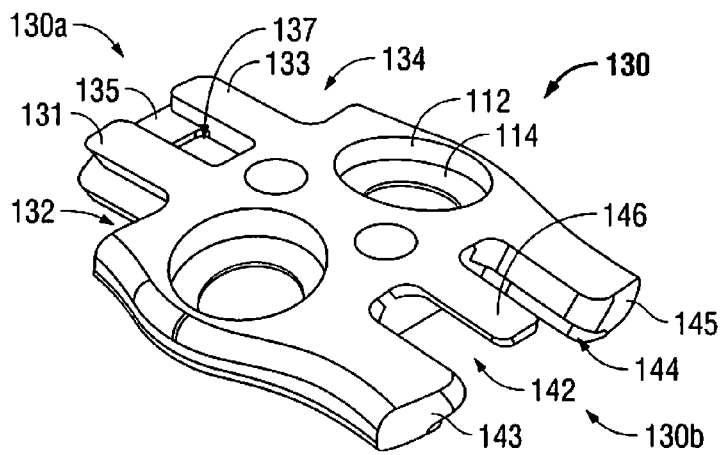
FIG. 5B is a perspective view of the middle section of FIG. 5A.
Figure 5C:
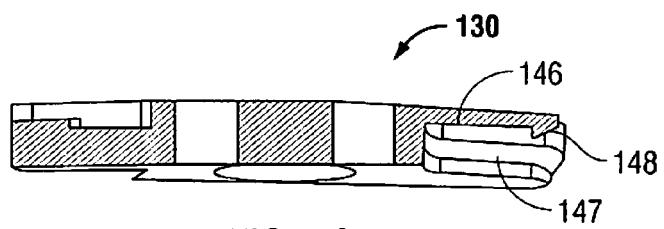
FIG. 5C is a side cross-sectional view of the middle section of FIG. 5A taken along section line 5C-5C.

The middle section 130 is described hereinafter with reference to FIGS. 5A-5C. On one end, the male end 130a, the middle section 130 includes bars 131, 133, each of which has a lateral bars 83, 85. A lip 135 extends transversely to the longitudinal axis and connects the distal ends of the bars 131, 133. A space 137 is defined between the bars 131, 133 and the lip 135. The bars 131, 133 include lateral bars 83, 85. Finger spaces 132, 134 are defined by the exterior side walls of the bars 131, 133, the lateral bars 83, 85, and stop flanges 136, 138. On the opposing female end 130b, receiving spaces 142, 144 are defined between a tongue 146 and fingers 143, 145. A tooth 148 extends downwards from tongue 146. A groove 147 is located in each of the receiving spaces 142, 144.

As assembled, the dynamic cervical plate 100 (FIGS. 1A, 1B, and 2) includes the first end section 110, the second end section 150, and the middle section 130. It is contemplated that additional middle sections 130 are included depending upon the particular procedure to be performed.

The receiving spaces 116, 118 of the first end section 110 are configured for slidably engaging with bars 131, 133 of the middle section 130. The tongue 115 slides between the bars 131, 133 such that the downwardly extending tooth 117 cantilevers over the lip 135, flexing the tongue 115. As the first end section 110 and the middle section 130 are brought into closer approximation, the tooth 117 passes over the lip 135 and enters the space 137. The tooth 117 has a flat portion that engages an edge of the lip 135 limiting the longitudinal movement of the first end section 110 relative to the middle section 130 (i.e. acts as a stop in one direction). The lateral bars 83, 85 slidably engage the groove 113. As such, the first end section 110 is repositionable with respect to the middle section 130. The gap 162 defined between the first end section 110 and the middle section 130 is variable.

The bars 149, 153 of the second end section 150 are configured for slidably engaging the receiving spaces 142, 146 of the middle section 130. The tongue 146 slides between the bars 149, 153 such that the downwardly extending tooth 148 cantilevers over the lip 157, flexing the tongue 146. As the second end section 150 and the middle section 130 are brought into closer approximation, the tooth 148 passes over the lip 157 and enters the space 155. The tooth 148 has a flat portion that engages an edge of the lip 157 limiting the longitudinal movement of the second end section 150 relative to the middle section 130 (i.e. acts as a stop). The lateral bars 94, 96 slidably engage the groove 147. As such, the second end section 150 is repositionable with respect to the middle section 130. The gap 164 defined between the second end section 150 and the middle section 130 is variable.

When the gaps 162, 164 are at a maximum value, the dynamic cervical plate 100 has a maximum overall length and defines the extended or second state. Conversely, when the gaps 162, 164 are at a minimum value, the dynamic cervical plate 100 has a minimum overall length and defines the collapsed or first state.

Operation of the dynamic cervical plate 100 will now be described in detail. The plate 100 comes preassembled as shown in FIG. 2. FIGS. 1A and 1B show the plate 100 in its completely collapsed state. The plate 100 may be delivered in the fully expanded state but the surgeon has the option to compress the plate 100 into closer approximation if it is open too much. The remaining gaps 162, 164, as illustrated in FIG. 2, will subside over time in vivo. Using a drill guide and screws, as are known in the art, the practitioner installs the dynamic cervical plate 100 across multiple vertebral bodies in the patient. The gaps 162, 164 are variable in response to relative movement between the first and second end sections 110, 150 with respect to the middle section 130. As the distance between the selected vertebral bodies decreases over time (i.e. subsidence), the first and second sections 110, 150 move relative to the middle section 130, thereby accommodating the subsidence without additional invasive procedures.

Figure 6:
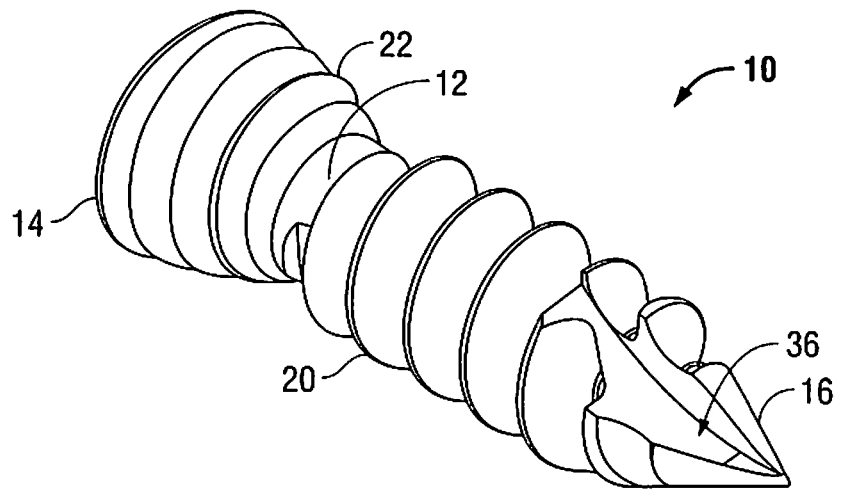
FIG. 6 is a perspective view of a self-starting screw.
Figure 7:
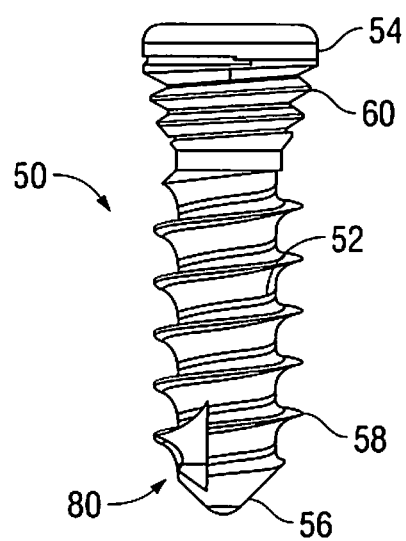
FIG. 7 is a side view of a self-tapping screw.

Referring now to FIGS. 6 and 7, a self-starting screw 10 (FIG. 6) and a self-tapping screw 50 (FIG. 7) are illustrated. The self-starting screw 10 has a shank 12, a tapered head portion 14 located at a proximal end of the shank 12 and a pointed tip portion 16 located at a distal end of the shank 12. The shank 12 has a uniform outer diameter and a first continuous helical thread 20 formed thereon. The first continuous helical thread 20 defines a cancellous bone thread. A second continuous thread 22 is formed on the head portion 14 and defines a thread thereon. The pitch of the first thread 20 is larger than the pitch of the second thread 22. The pitch of the second thread 22 changes halfway down the head 14. The bottom half of the second thread 22 may be half the pitch of the first thread 20. Further down, the pitch of the second thread 22 may change to less than half of the pitch of the first thread 20. The self-starting screw 10 further includes a self-starting portion that extends proximally from the pointed tip portion 16. The self-starting portion includes first and second sidewalls that define a flute section 36. The first and second sidewalls of the flute section 36 extend from the pointed tip 16 to a second crest of cancellous bone thread 20.

The self-tapping screw 50 includes a shank 52, a tapered head portion 54 located at a proximal end of the shank 52, and a rounded tip portion 56 located at a distal end of the shank 52. The shank 52 has a uniform outer diameter and a first continuous helical thread 58 formed thereon. The first continuous helical thread 58 defines cancellous bone thread. A second continuous thread 60 is formed on the head portion 54 and defines a thread thereon. The pitch of the first thread 58 is larger than the pitch of the second thread 60. Each of the threads 58, 60 has a uniform pitch. The self-tapping screw 50 includes a self-tapping portion that extends proximally from the rounded tip portion 56. The self-tapping portion includes first and second sidewalls that define a flute section 80. The first and second sidewalls of the flute section 80 extend from the rounded tip 56 towards the second crest of cancellous bone thread 58. Each of the screws 10, 50 is formed from a suitable biocompatible material such as Ti-6AL-4V alloy. Alternatively, it is contemplated that other suitable biocompatible materials are used to form the screws 10, 50.

Referring additionally to FIG. 1B, the lip 114 is configured for engaging the screw 10, 50 such that rotating the screw 10, 50 causes the threads of the head 14, 54 of the respective screw 10, 50 to engage the lip 114 and form threads thereon such that each screw 10, 50 is secured in the screw opening 110 and resists backing out of the screw opening 110. Since the material of the respective section 110, 130, 150 is softer than the material of the screw 10, 50, the threads on the screw 10, 50 may engage the lip 114 as the screw 10, 50 is inserted into the opening 104, thereby minimizing the screw 10, 50 from backing out during normal usage. The threads of the screw 10, 50 engage the lip 114 when the screw 10, 50 is in various angular orientations with respect to the axis of the screw opening 110. A suitable screw and locking mechanism for use in the dynamic cervical plate 100 are disclosed in U.S. Pat. No. 6,322,562 to Wolter, the entire contents of which are hereby incorporated by reference, although other mechanisms for locking the screw to the dynamic cervical plate 100 are contemplated.

An alternate embodiment of the dynamic cervical plate is shown in FIGS. 8A-11B and is referred to as dynamic cervical plate 200. In this embodiment, the first end section 210 is interconnected to the middle section 230 by a first pin 178a through a pin hole 175 disposed on the distal end of a tongue 215 of the first end section 210 and through a slide cavity 238 of the middle section 230 which extends transaxially through a partition 232 and a platform 231 of middle section 230. The second end section 250 is interconnected to the middle section 230 by a second pin 178b through a pin hole 225 disposed on the distal end of a tongue 246 of the middle section 230 and through a slide cavity 201 of the second end section 250 which extends transversely to the longitudinal axis through a partition 192 and a platform 190 of second end section 250. Furthermore, teeth 176, 217 disposed on the distal end of the tongue 215 of the first section 210 interconnect with a tongue space 242 and ridges 240 of one end 230a of the middle section 230. Similarly, a tongue 246 on the opposing end 230b of the middle section 230 having teeth 48, 226 disposed on the distal end thereof interconnect with a tongue space 204 and ridges 202 of the second end section 250. The pins 178a, 178b limit the maximum size of the plate 200, lengthwise. The plate 200, however, can get shorter, but not longer. In other words, the pins 178a, 178b are forwardly slidable in the slide cavities 201, 238, but as the teeth 176, 217, 148, 226 interlock with the ridges 202, 240, rearward sliding is minimized, and thus, lengthening is minimized. As discussed above, screws 10, 50 are likewise compatible with this embodiment.

Figure 9A:
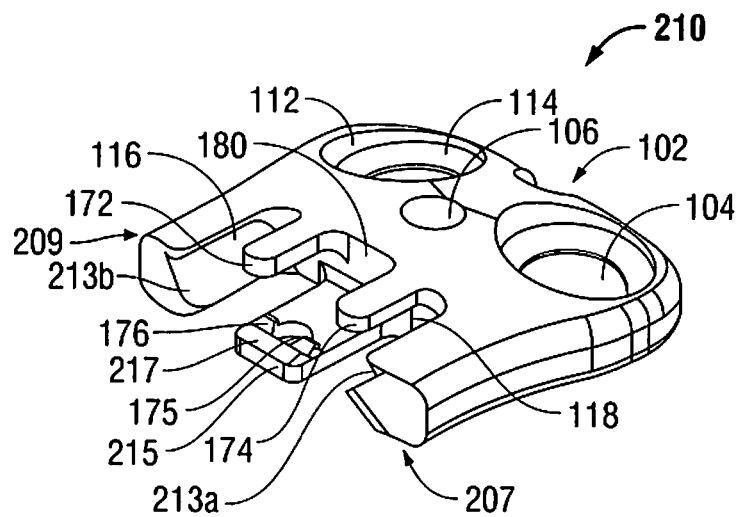
FIG. 9A is a top perspective view of the first end section of the dynamic cervical plate of FIG. 8A.
Figure 9B:
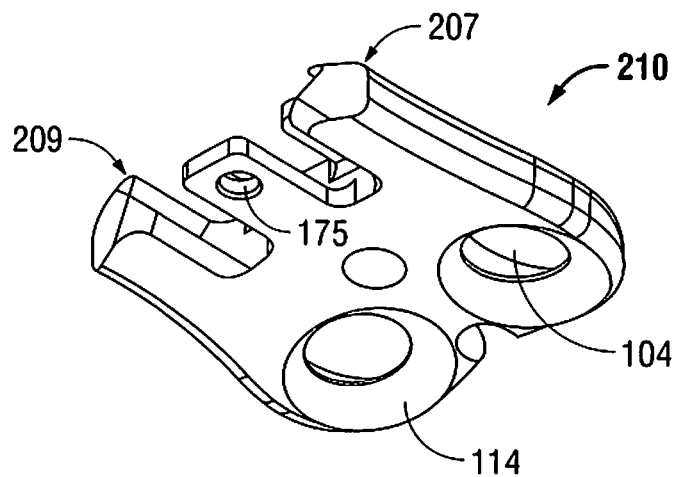
FIG. 9B is a bottom perspective view of the first end section of FIG. 9A.

In FIGS. 9A-9B, details of the first end section 210 of the dynamic cervical plate 200 are illustrated. The first end section 210 includes a tongue 215, bars 172, 174, and fingers 207, 209 that extend longitudinally. The tongue 215, bars 172, 174, and fingers 207, 209 define receiving spaces 116, 118, and 180. A first tooth 217 extends upwards from the distal end of the tongue 215. A second tooth 176 extends upwards from the distal end of the tongue 215 adjacent to the first tooth 217. A pin hole 175 extends transversely to the longitudinal axis through the center of the second tooth 176 and the tongue 215 at the distal end of the tongue 215 for receiving the pin 178. Grooves 213a, 213b are defined by the interior surface of the fingers 207, 209. The tongue 215 is flexibly connected to the first end section 210 and is adapted to move above and below the plane defined by the lower surface of the first end section 210. The interaction between the first end section 210 and the middle section 230 will be discussed in further detail hereinbelow.

Figure 10A:
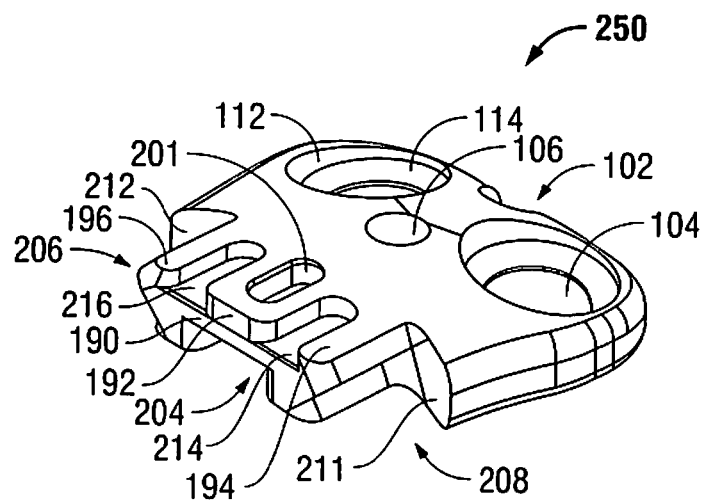
FIG. 10A is a top perspective view of the second end section of the dynamic cervical plate of FIG. 8A.
Figure 10B:
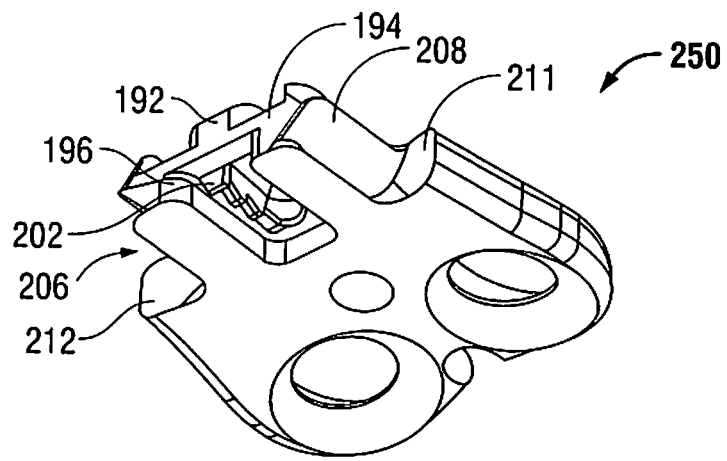
FIG. 10B is a bottom perspective view of the second end section of FIG. 10A.

In FIGS. 10A-10B, details of the second end section 250 of the dynamic cervical plate 200 are shown. The second end section 250 includes a platform 190, a partition 192 and bars 194, 196 that extend along the longitudinal axis of the second end section 250. A slide cavity 201 having elliptical outer boundaries extends transversely to the longitudinal axis through the center of the partition 192 and the platform 190 for receiving the pin 178. A plurality of ridges 202 extends downward from the underside of the platform 190 and is disposed about the slide cavity 201. A tongue space 204 is defined by the underside of the platform 190, the lower portion of interior side walls of the bars 194, 196 and ridges 202. Bar spaces 214, 216 are defined by the exterior sides of the partition 192, the interior side walls of the upper portion of the bars 194, 196, and the top surface of the platform 190. Finger spaces 206, 208 are defined by the exterior sidewalls of the bars 194, 196 and stop flanges 211, 212 abutting the body of the second end section 250. The interaction between the second end section 250 and the middle section 230 of the dynamic cervical plate 200 will be discussed in further detail hereinbelow.

Figure 11A:
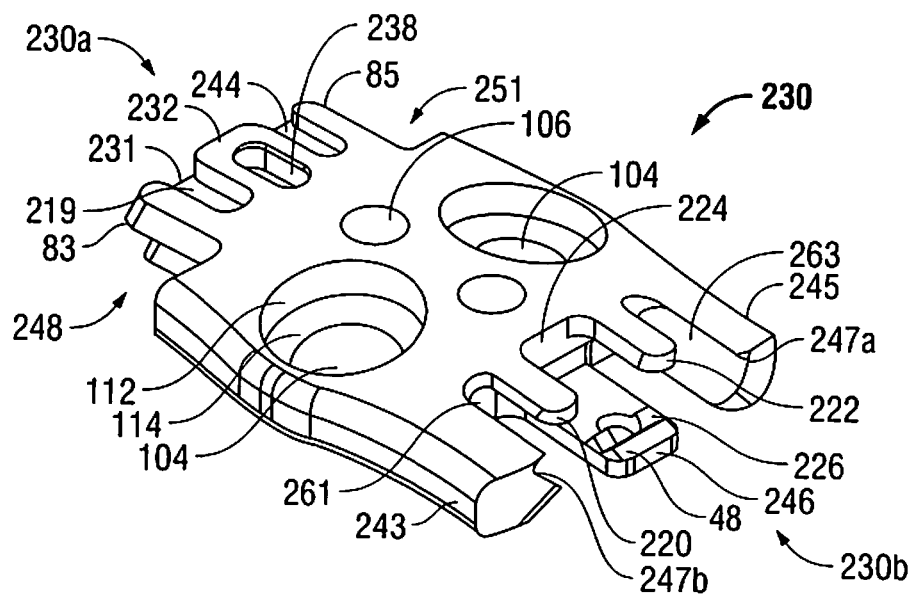
FIG. 11A is a top perspective view of the middle section of the dynamic cervical plate of FIG. 8A.
Figure 11B:
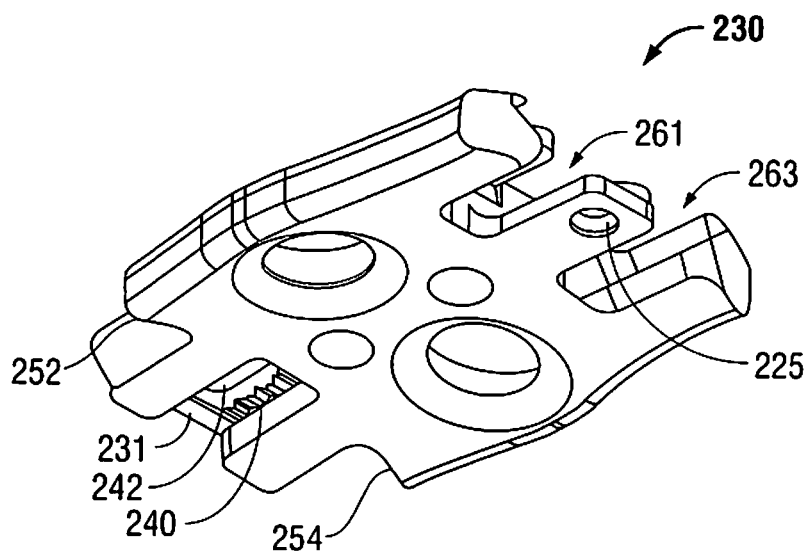
FIG. 11B is a bottom perspective view of the middle section of FIG. 11A.

Details of the middle section 230 of the dynamic cervical plate 200 are described hereinafter with reference to FIGS. 11A-11B. The female end 230b of the middle section 230 includes a tongue 246, bars 220, 222, and fingers 243, 245 that extend longitudinally. The tongue 246, bars 220, 222, and fingers 243, 245 define receiving spaces 261, 263, and 224. A first tooth 48 extends upwards from the distal end of the tongue 246. A second tooth 226 extends upwards from the distal end of the tongue 246 adjacent to the first tooth 48. A pin hole 225 extends transversely to the longitudinal axis through the center of the second tooth 226 and the tongue 246 at the distal end of the tongue 246. Grooves 247a, 247b are defined by the interior walls of the fingers 243, 245. The tongue 246 is flexibly connected to the middle section 230 and is adapted to move above and below the plane defined by the lower surface of the middle section 230.

On the opposing male end 230a of the middle section 230 of the dynamic cervical plate 200, a platform 231, a partition 232 and bars 83, 85 extend along the longitudinal axis of the middle section 230. A slide cavity 238 having elliptical outer boundaries extends transversely to the longitudinal axis through the center of the partition 232 and the platform 231. A plurality of ridges 240 extend downward from the underside of the platform 231. A tongue space 242 is defined by the underside of the platform 231, the interior walls of the lower portion of the bars 83, 85, and the ridges 240. Bar spaces 244, 219 are defined by the exterior side walls of the partition 232, the interior sidewalls of the upper portion of the bars 83, 85, and the top surface of the platform 231. Finger spaces 248, 251 are defined by the exterior sidewalls of the bars 83, 85 and stop flanges 252, 254 abutting the body of the middle section 130.

Referring again to FIG. 8B, the pin 178, includes a base 270 and a cap 272, each of which can be substantially cylindrical. The base 270 and the cap 272 are interconnected by a shoulder 271. The cap 272 is configured to engage the slide cavity 201 of the second end section 250 and slide cavity 238 of middle section 230. The base 270 is configured to engage the pin hole 175 of first end section 210 and the pin hole 225 of the middle section 230. As described above, this embodiment also includes an orifice 106, a notch 102, and plurality of openings 105 with a lip 114 on each section for receiving a screw 10, 50.

Operation of this embodiment of the dynamic cervical plate 200 will now be described in detail. The pins 178a, 178b are inserted through pin holes 175, 225, to interconnect with the slide cavities 201, 238 which enable the first and second end sections 210, 250 to adjust relative to the middle section 230. When the pins 178a, 178b interconnect the sections 210, 230, 250, the pins 178a, 178b provide a minimum and maximum longitudinal length of the cervical plate 200 when the pins 178a, 178b engage the distal or proximal ends of the slide cavities 201, 238 relative to the center of the dynamic cervical plate 200. Furthermore, teeth 176, 217 disposed on the distal end of the tongue 215 of the first section 210 interconnect with the tongue space 242 and ridges 240 of one end 230a of the middle section 230. Similarly, the tongue 246 on the opposing end 230b of the middle section 230 having teeth 48, 226 disposed on the distal end thereof interconnect with the tongue space 204 and ridges 202 of the second end section 250. The pins 178a, 178b limit the maximum size of the plate 200, lengthwise. The plate 200, however, can get shorter, but not longer. The pins 178a, 178b are forwardly slidable in the slide cavities 201, 238. However, as the teeth 176, 217, 48, 226 cantilever over the ridges 202, 240 when the sections are brought in closer approximation, the teeth 176, 217, 148, 226 interlock with the ridges 202, 240. Thus, rearward sliding and longitudinal expansion (lengthening) is minimized. In other words, the pins 178 define a maximum length of the plate 200 while allowing for subsidence and inhibiting expansion or lengthening of the plate 200 once installed.

The dynamic cervical plate 200 comes preassembled in an open state (FIG. 8A). It is compressible to a completely collapsed state (no gaps 262, 264). The surgeon has the option to compress the plate 200 into closer approximation if it is open too much. The remaining gaps 262, 264 will subside over time in vivo. The practitioner adjusts the first end section 210 and the second end section 250 with respect to the middle section 230, thereby defining the gaps 262, 264 for the procedure being performed. Using a drill guide and screws, as are known in the art, the practitioner installs the dynamic cervical plate 200 across multiple vertebral bodies in the patient. The gaps 262, 264 are variable in response to relative movement between the first and second end sections 210, 250 with respect to the middle section 230. As the distance between the selected vertebral bodies decreases over time (i.e. subsidence), the first and second sections 210, 250 move relative to the middle section 130, thereby accommodating the subsidence without additional invasive procedures. The gaps 262, 264 are thus variable. It is contemplated that additional middle sections 230 are included depending upon the particular procedure to be performed.

Figure 12A:
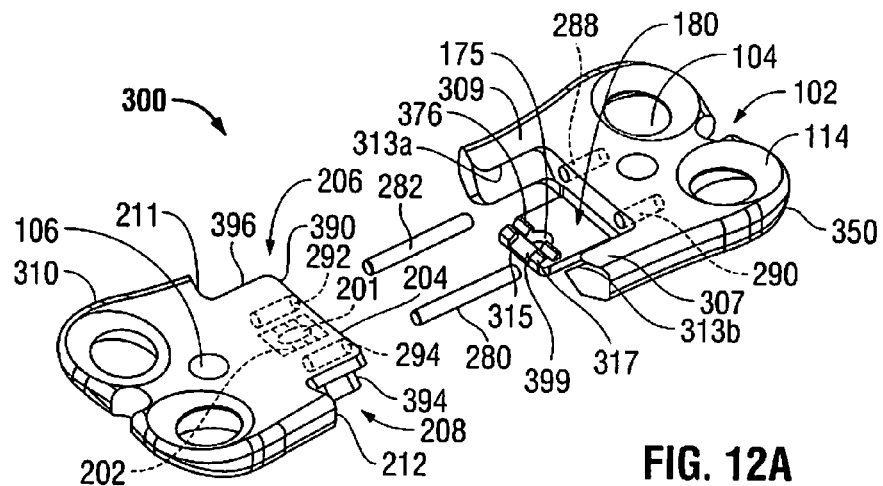
FIG. 12A is an exploded perspective view, with parts separated, of a further embodiment of the dynamic cervical plate in accordance with the present disclosure.
Figure 12B:
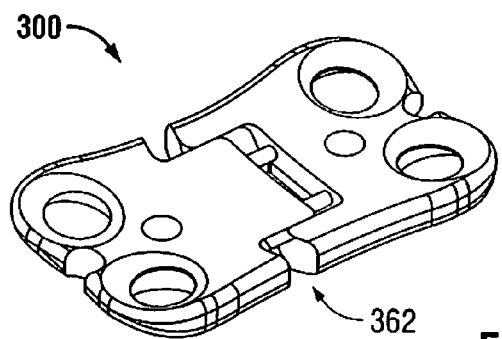
FIG. 12B is a bottom perspective view of the dynamic cervical plate of FIG. 12A in a first state.
Figure 12C:
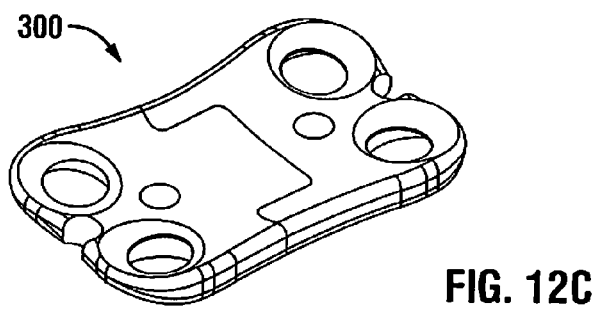
FIG. 12C is a bottom perspective view of the dynamic cervical plate of FIG. 12A in a second state.

An alternate embodiment of the dynamic cervical plate is shown in FIGS. 12A-12C and is referred to as dynamic cervical plate 300. The first end section 310 includes a platform 390 that extends along the longitudinal axis thereof. A slide cavity 201 having elliptical outer boundaries extends transversely to the longitudinal axis disposed within the center of the platform 390 for receiving the interlocking pin 178. A plurality of ridges 202 extend downward from the underside of the slide cavity 201 about the perimeter thereof. A tongue space 204 is defined by the underside of the platform 390, the interior side walls of the lower portion of the bars 394, 396, and the ridges 202. Finger spaces 206, 208 are defined by the exterior sidewalls of the bars 394, 396, platform 390 and stop flanges 211, 212 abutting the body of the first end section 310. First and second support bar cavities 292, 294 are longitudinally disposed in the distal end of the platform 390 in spaced-apart relation relative to the longitudinal axis for receiving first and second support bars 280, 282.

From FIGS. 12A-12C, the second end section 350 includes first and second fingers 307, 309 and a tongue 315 that extend longitudinally. A receiving space 180 is defined therebetween. First and second fingers 307, 309 have grooves 313a, 313b disposed on the interior walls thereof. A first tooth 317 extends upwards from the distal end of the tongue 315 and has a space 399 therebetween. A second tooth 376 extends upwards from the distal end of the tongue 315 adjacent to the first tooth 317. A pin hole 175 extends transversely to the longitudinal axis through the center of the second tooth 376 and the tongue 315 at the distal end of the tongue 315 for receiving the interlocking pin 178. The tongue 315 is flexibly connected to the second end section 350 and is adapted to move above and below the plane defined by the lower surface of the second end section 350. Furthermore, first and second support bar cavities 288, 290 are longitudinally disposed in the distal end of the body of the second section 350 in spaced-apart relation relative to the longitudinal axis for receiving first and second support bars 280, 282. As described above, this embodiment also includes an orifice 106, a notch 102, and a plurality of openings 105 with a lip 114 on each section for receiving a screw 10, 50.

Operation of the dynamic cervical plate 300 will now be described in detail. The second end section 350 is positioned to receive first and second support bars 280, 282 in first and second support bar cavities 288, 290. Alternatively, the first end section 310 is positioned to receive first and second support bars 280, 282 in first and second support bar cavities 292, 294. The support bars 280, 282 provide lateral support and minimize excess flexure between the sections 310, 350. Second end section 350 is then connected to first end section 310 having the first and second support bars 280, 282 connected therebetween and disposed in first and second support bar cavities 288, 290 of second end section 350 and first and second support bar cavities 292, 294 of first end section 310. The tongue 315 engages the tongue space 204 and the teeth 317, 376 interconnect with the ridges 202. The pin 178 is inserted through the pin hole 175 and interconnects with the slide cavity 201. When the pin 178 interconnects the sections 310, 350, the pin 178 sets a maximum longitudinal length of the cervical plate 300. The plate 300, however, can get shorter, but not longer. The pin 178 is forwardly slidable in the slide cavity 201. However, as the teeth 376, 317 cantilever over the ridges 202 when the sections are brought in closer approximation, the teeth 376, 317 interlock with the ridges 202. Thus, rearward sliding and longitudinal expansion (lengthening) is minimized. In other words, the pin 178 defines a maximum length of the plate 300 while allowing for subsidence and inhibiting expansion or lengthening of the plate 300 once installed. The gap 362 is thus variable. As discussed above, screws 10, 50 are likewise compatible with this embodiment.

The dynamic cervical plate 300 comes preassembled in an open state (FIG. 12B). It may be compressed to a completely collapsed state (FIG. 12C). The surgeon has the option to compress the plate 300 into closer approximation if it is open too much. The remaining gap 362 will subside over time in vivo. The practitioner adjusts the first end section 310 and the second end section 350 with respect to one another, thereby defining a gap 362, the distance of which is dependant upon the patient and procedure being performed. In some situations, the surgeon may wish to provide a maximum overall length of the cervical plate 300. In other situations, a minimum or intermediate position is more appropriate. Using a drill guide and screws, as are known in the art, the practitioner installs the dynamic cervical plate 300 across multiple vertebral bodies in the patient. The gap 362 is variable in response to relative movement between the first and second end sections 310, 350 with respect to each other. As the distance between the selected vertebral bodies decreases over time (i.e. subsidence), the first and second sections 310, 350 move relative to each other, thereby accommodating the subsidence without additional invasive procedures.

Figure 13A:
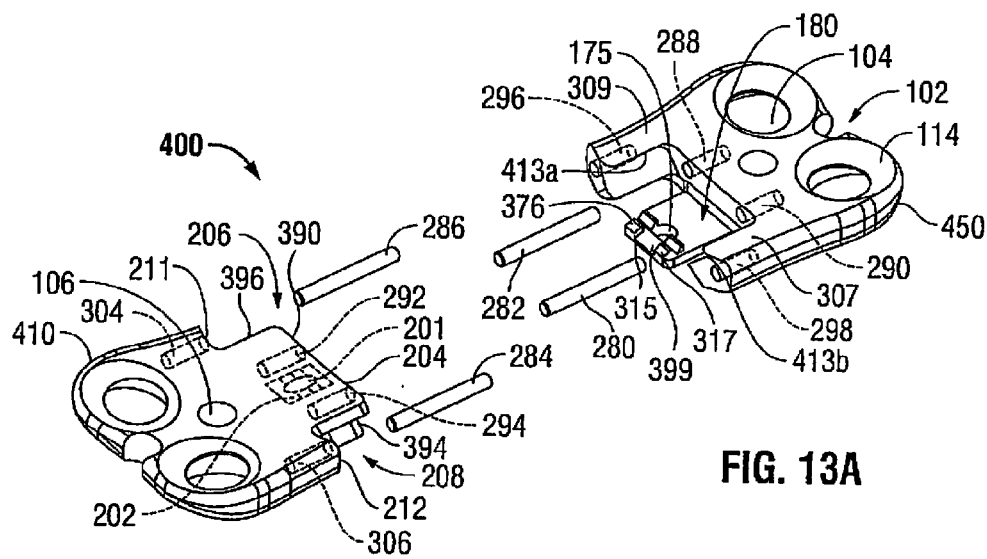
FIG. 13A is an exploded perspective, with parts separated, view of another embodiment of the dynamic cervical plate in accordance with the present disclosure.
Figure 13B:
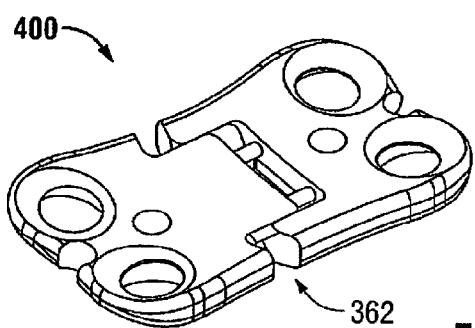
FIG. 13B is a bottom perspective view of the dynamic cervical plate of FIG. 13A in a first state.
Figure 13C:
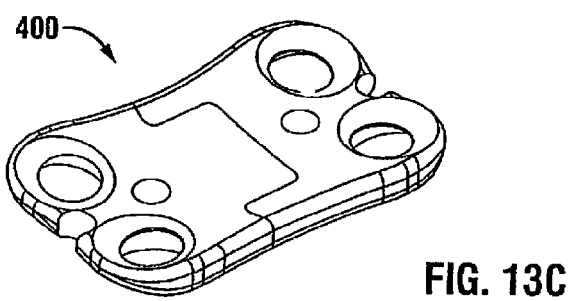
FIG. 13C is a bottom perspective view of the dynamic cervical plate of FIG. 13A in a second state.

An alternate embodiment of the dynamic cervical plate is shown in FIGS. 13A-13C and is referred to as dynamic cervical plate 400. In this embodiment, the first end section 410 is interconnected to the second end section 450. This embodiment discloses first, second, third, and fourth support bars 280, 282, 284, 286 coupling first end section 410 to second end section 450.

The dynamic cervical plate 400 has a first end section 410 that includes a platform 390 that extends along the longitudinal axis of the first end section 410. A slide cavity 201 having elliptical outer boundaries extends transversely to the longitudinal axis disposed within the center of the partition platform 390 for receiving the pin 178. Dynamic cervical plate 400 has a plurality of ridges 202 that extend downward from the underside of the platform 390 and are disposed about the underside of the slide cavity 201 around the perimeter thereof. A tongue space 204 is defined by the underside of the platform 390, the interior side walls of the lower portion of the bars 394, 396 disposed on the underside of the platform 390, and the ridges 202. Finger spaces 206, 208 are defined by the exterior sidewalls of the bars 394, 396, the platform 390 and the stop flanges 211, 212 abutting the body of the first end section 410. First and second support bar cavities 292, 294 are longitudinally disposed in the distal end of the platform 390 in spaced-apart relation relative to the longitudinal axis for receiving first and second support bars 280, 282. Third and fourth support bar cavities 304, 306 are longitudinally disposed in first and second stop flanges 211, 212 for receiving third and fourth support bars 286, 284.

The second end section 450 of dynamic cervical plate 400 includes first and second fingers 307, 309 and a tongue 315 that extend longitudinally and define the receiving space 180 therebetween. First and second fingers 307, 309 have groove 413a, 413b disposed on the interior walls thereof. A first tooth 317 extends upwards from the distal end of the tongue 315. A second tooth 376 also extends upwards from the distal end of the tongue adjacent to the first tooth 317. A pin hole 175 extends transversely to the longitudinal axis through the center of the second tooth 376 and the tongue 315 at the distal end of the tongue 315 for receiving the pin 178. The tongue 315 is flexibly connected to the second end section 450 and is adapted to move above and below the plane defined by the lower surface of the second end section 450. Furthermore, first and second support bar cavities 288, 290 are longitudinally disposed in the distal end of the body of the second section 450 in spaced-apart relation relative to the longitudinal axis for receiving first and second support bars 280, 282. Third and fourth support bar cavities 296, 298 are longitudinally disposed in the distal end of first and second fingers 307, 309 for receiving third and fourth support bars 284, 286. As described above, this embodiment also includes an orifice 106, a notch 102, and plurality of openings 105 with a lip 114 on each section for receiving a screw 10, 50.

Operation of dynamic cervical plate 400 will now be described in detail. The second end section 450 is positioned to receive first, second, third, and fourth support bars 280, 282, 284, 286 in first, second, third, and fourth support bar cavities 288, 290, 296, 298. Alternatively, the first end section 410 is positioned to receive first, second, third and fourth support bars 280, 282, 284, 286 in first, second, third and fourth support bar cavities 292, 294, 304, 306. The support bars 280, 282, 284, 286 provide lateral support and minimize excess flexure between sections 410, 450. Second end section 450 is connected to first end section 410 having the first, second, third and fourth support bars 280, 282, 284, 286 connected therebetween and disposed in their respective support bar cavities 288, 290, 296, 298 of second end section 150 and support bar cavities 292, 294, 304, 306 of first end section 410. The tongue 315 engages the tongue space 204 and the teeth 317, 376 interconnect with the ridges 202. The pin 178 is inserted through the pin hole 175 and interconnects with the slide cavity 201. When the pin 178 interconnects the sections 310, 350, the pin 178 sets a maximum longitudinal length of the cervical plate 400. The plate 400, however, can get shorter, but not longer. The pin 178 is forwardly slidable in the slide cavity 201. However, as the teeth 376, 317 cantilever over the ridge 202 when the sections are brought into closer approximation, the teeth 376, 317 interlock with the ridges 202. Thus, rearward sliding and longitudinal expansion (lengthening) is minimized. In other words, the pin 178 defines a maximum length of the plate 400 while allowing for subsidence and inhibiting expansion or lengthening of the plate 400 once installed. The gap 362 is thus variable. As discussed above, screws 10, 50 are likewise compatible with this embodiment.

The dynamic cervical plate 400 (FIG. 13A) comes preassembled in an open state (FIG. 13B). It is compressible to a completely collapsed state (FIG. 13C). The surgeon has the option to compress the plate 400 into closer approximation if it is open too much. The remaining gap 362 will subside over time in vivo. The practitioner adjusts the first end section 410 and the second end section 450 with respect to one another, thereby defining a gap 362 the distance of which is dependant upon the patient and procedure being performed. In other words, in some situations, the surgeon may wish to provide a maximum overall length of the cervical plate 400. In other situations, a minimum or intermediate position is more appropriate. Using a drill guide and screws, as are known in the art, the practitioner installs the dynamic cervical plate 400 across multiple vertebral bodies in the patient. The gap 362 is variable in response to relative movement between the first and second end sections 410, 450 with respect to each other. As the distance between the selected vertebral bodies decreases over time (i.e. subsidence), the first and second sections 410, 450 move relative to each other, thereby accommodating the subsidence without additional invasive procedures. As described above, this embodiment also includes an orifice 106, a notch 102, and plurality of openings 105 with a lip 114 on each section for receiving a screw 10, 50.

Figure 14:
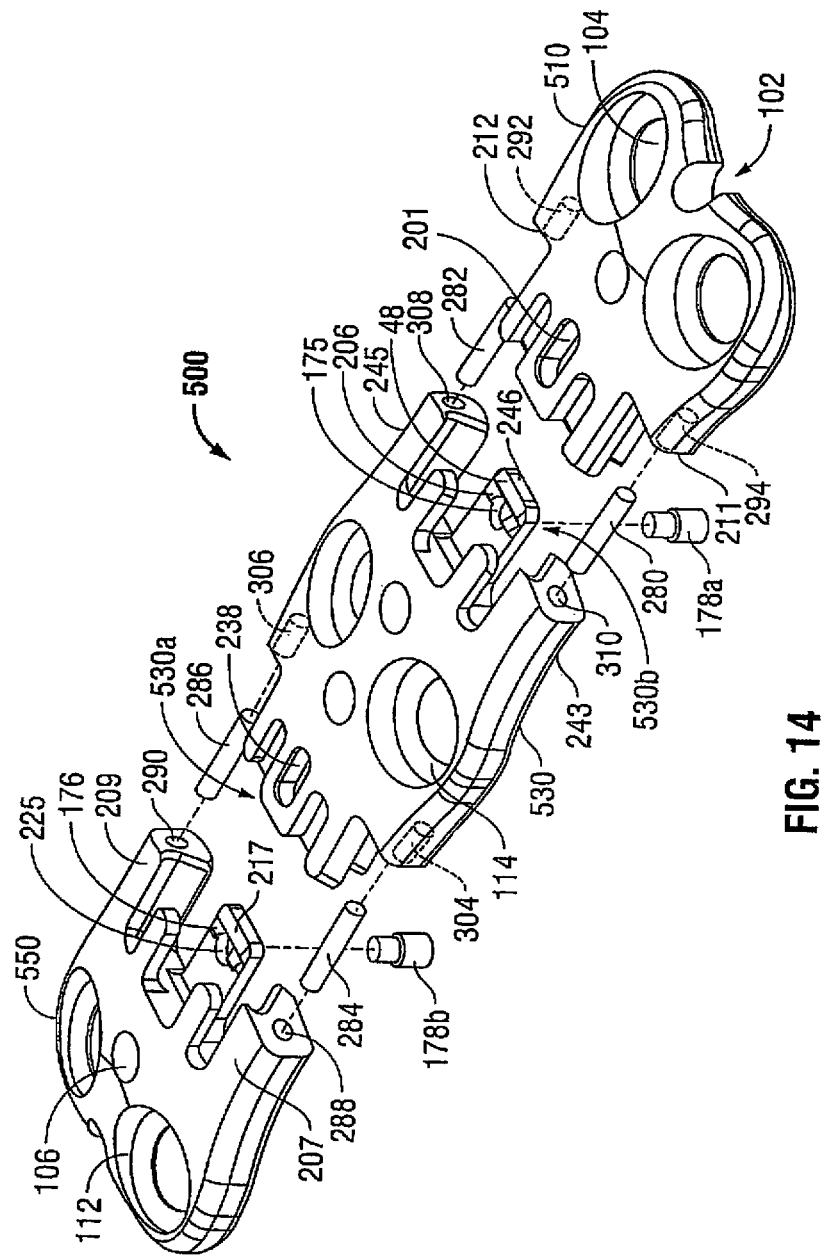
FIG. 14 is an exploded perspective view, with parts separated, of one embodiment of a dynamic cervical plate in accordance with the present disclosure.

An alternate embodiment of the dynamic cervical plate is shown in FIG. 14 and is referred to as dynamic cervical plate 500. In this embodiment, the first end section 510 is interconnected to the middle section 530 which is connected to a second end section 550. The dynamic cervical plate 500 contemplated in this embodiment teaches a first and a second support bar 280, 282 coupling first end section 510 to the middle section 530 and a third and fourth support bar 284, 286 coupling the middle section 530 to the second end section 550. The support bars 280, 282, 284, 286 provide lateral support and minimize excess flexure between sections 510, 530, 550. The first end section 510 has support cavities 294, 292 longitudinally disposed in first and second stop flanges 211, 212 for receiving first and second support bars 280, 282. The middle section 530 has first and second support cavities 308, 310 longitudinally disposed in the distal end of the first and second fingers 243, 245 for receiving first and second support bars 280, 282. The middle section 530 also has third and fourth support cavities 304, 306 for receiving third and fourth support bars 284, 286. The second end section 550 has first and second support cavities 288, 290 longitudinally disposed in the distal end of the first and second fingers 207, 209 for receiving third and fourth support bars 284, 286. The first end section 510 and the middle section 530 as well as the middle section 530 and the second end section 550 are interconnected by pins 178a, 178b. As described above, this embodiment also includes an orifice 106, a notch 102, and plurality of openings 105 with a lip 114 on each section for receiving a screw 10, 50.

Operation of this embodiment of the dynamic cervical plate 500 will now be described in detail. First end section 510, second end section 550 and middle section 530 are all positioned relative to one another for receiving support bars 280, 282, 284, 286. The support bars 280, 282, 284, 286 are inserted into their respective support bar cavities 288, 290, 292, 294, 304, 306, 308, 310 of sections 510, 530, 550. The support bars 280, 282, 284, 286 provide lateral support and minimize excess flexure between sections 510, 550. The pins 178a, 178b are inserted through pin holes 175, 225 and interconnected with slide cavities 201, 238. Furthermore, teeth 176, 217 disposed on the distal end of the tongue 215 of the second section 550 interconnect with the tongue space 242 and ridges 240 of one end 530a of the middle section 530. Similarly, the tongue 246 on the opposing end 530b of the middle section 530 having teeth 148, 226 disposed on the distal end thereof interconnect with the tongue space 204 and ridges 202 of the first end section 510. The pins 178a, 178b limit the maximum size of the plate 500, lengthwise. The plate 500, however, can get shorter, but not longer. The pins 178a, 178b are forwardly slidable in the slide cavities 201, 238. However, as the teeth 176, 217, 48, 226 cantilever over the ridges 202, 240 when the sections are brought in closer approximation, the teeth 176, 217, 48, 226 interlock with the ridges 202, 240. Thus, rearward sliding and longitudinal expansion (lengthening) is minimized. In other words, the pins 178 define a maximum length of the plate 500 while allowing for subsidence and inhibiting expansion or lengthening of the plate 500 once installed. The gaps 262, 264 are thus variable. As discussed above, screws 10, 50 are likewise compatible with this embodiment.

The dynamic cervical plate 500 comes preassembled in an open state. It is compressible to a completely collapsed state. The surgeon has the option to compress the plate 500 into closer approximation if it is open too much. The remaining gaps 262, 264 will subside over time in vivo. The practitioner adjusts each of the sections 510, 530, 550 with respect to one another, thereby defining gaps 262, 264, the gap distances being dependant upon the patient and procedure being performed. In some situations, the surgeon may wish to provide a maximum overall length of the cervical plate 500. In other situations, a minimum or intermediate position is more appropriate. Using a drill guide and screws, as are known in the art, the practitioner installs the dynamic cervical plate 500 across multiple vertebral bodies in the patient. The gaps 262, 264 are variable in response to relative movement between the sections 510, 530, 550 with respect to each other. As the distance between the selected vertebral bodies decreases over time (i.e. subsidence), the sections 510, 530, 550 move relative to each other, thereby accommodating the subsidence without additional invasive procedures. It is contemplated that additional middle sections 530 are included depending upon the particular procedure to be performed.

Figure 15:
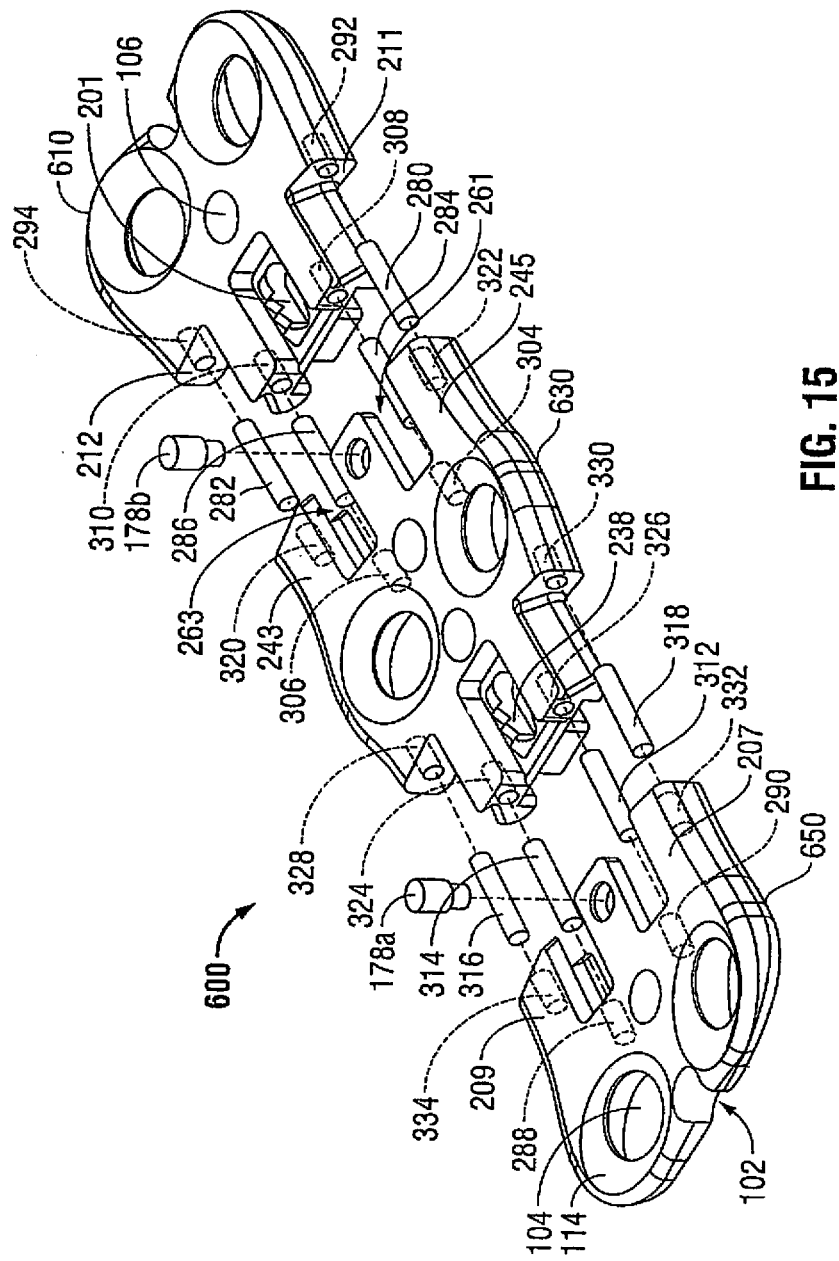
FIG. 15 is an exploded perspective view, with parts separated, of another embodiment of the dynamic cervical plate in accordance with the present disclosure.

An alternate embodiment of the dynamic cervical plate is shown in FIG. 15 and is referred to as dynamic cervical plate 600. In this embodiment, the first end section 610 is interconnected to the middle section 630 which is connected to a second end section 650. The dynamic cervical plate 600 contemplated in this embodiment teaches first, second, third, and fourth support bars 280, 282, 284, 286 coupling first end section 610 to the middle section 630 and fifth, sixth, seventh, and eighth support bars 312, 314, 316, 318 coupling the middle section 630 to the second end section 650. The first end section 610 has support cavities 294, 292 longitudinally disposed in first and second stop flanges 211, 212 for receiving first and second support bars 280, 282. The first end section 610 also has support cavities 308, 310 longitudinally disposed through the distal end thereof. The middle section 630 has first and second support cavities 320, 322 longitudinally disposed in the distal end of first and second fingers 243, 245 for receiving first and second support bars 280, 282. Additionally, third and fourth support bar cavities 304, 306 are disposed in the proximal end of the receiving spaces 261, 263 in the middle section 630 for receiving third and fourth support bars 284, 286. The middle section 130 also has fifth and sixth support cavities 324, 326 for receiving fifth and sixth support bars 312, 314. Additionally, the middle section 630 has seventh and eighth support cavities 328, 330 for receiving seventh and eighth support bars 316, 318. The second end section 650 has first and second support cavities 288, 290 longitudinally disposed in the distal end of the first and second fingers 207, 209 for receiving seventh and eighth support bars 316, 318. Additionally, the second end section 650 has third and fourth support cavities 332, 334 for receiving fifth and sixth support bars 312, 314. The first end section 610 and the middle section 630 as well as the middle section 630 and the second end section 650 are interconnected by pins 178a, 178b. As described above, this embodiment also includes an orifice 106, a notch 102, and plurality of openings 105 with a lip 114 on each section for receiving a screw 10, 50.

Operation of this embodiment of the dynamic cervical plate 600 will now be described in detail. First end section 610, second end section 650 and middle section 630 are all positioned relative to one another for receiving support bars 280, 282, 284, 286, 312, 314, 316, 318. The support bars 280, 282, 284, 286, 312, 314, 316, 318 are inserted into their respective support bar cavities 288, 290, 292, 294, 304, 306, 308, 310, 320, 322, 324, 326, 328, 330, 332, 334 of sections 110, 130, 150. The support bars 280, 282, 284, 286, 312, 314, 316, 318 provide lateral support and minimize excess flexure between sections 610, 630, 650. The pins 178a, 178b are inserted through pin holes 175, 225 and interconnect with slide cavities 201, 238. Furthermore, teeth 176, 217 disposed on the distal end of the tongue 215 of the second end section 650 interconnect with the tongue space 242 and ridges 240 of one end 630a of the middle section 630. Similarly, the tongue 246 on the opposing end 630b of the middle section 630 having teeth 48, 226 disposed on the distal end thereof interconnect with the tongue space 204 and ridges 202 of the first end section 610. The pins 178a, 178b limit the maximum size of the plate 600, lengthwise. The plate 600, however, can get shorter, but not longer. The pins 178a, 178b are forwardly slidable in the slide cavities 201, 238. However, as the teeth 176, 217, 48, 226 cantilever over the ridges 202, 240 when the sections are brought in closer approximation, the teeth 176, 217, 48, 226 interlock with the ridges 202, 240. Thus, rearward sliding and longitudinal expansion (lengthening) is minimized. In other words, the pins 178 define a maximum length of the plate 600 while allowing for subsidence and inhibiting expansion or lengthening of the plate 600 once installed. The gaps 262, 264 are thus variable. As discussed above, screws 10, 50 are likewise compatible with this embodiment.

The dynamic cervical plate 600 comes preassembled in an open state. It is compressible to a completely collapsed state. The surgeon has the option to compress the plate 600 into closer approximation if it is open too much. The remaining gaps 262, 264 will subside over time in vivo. The practitioner adjusts each of the sections 610, 630, 650 with respect to one another, thereby defining gaps 262, 264, the gap distances being dependant upon the patient and procedure being performed. In some situations, the surgeon may wish to provide a maximum overall length of the cervical plate 600. In other situations, a minimum or intermediate position is more appropriate. Using a drill guide and screws, as are known in the art, the practitioner installs the dynamic cervical plate 600 across multiple vertebral bodies in the patient. The gaps 262, 264 are variable in response to relative movement between the sections 610, 630, 650 with respect to each other. As the distance between the selected vertebral bodies decreases over time (i.e. subsidence), the sections 610, 630, 650 move relative to each other, thereby accommodating the subsidence without additional invasive procedures. It is contemplated that additional middle sections 630 are included depending upon the particular procedure to be performed.

Figure 16:
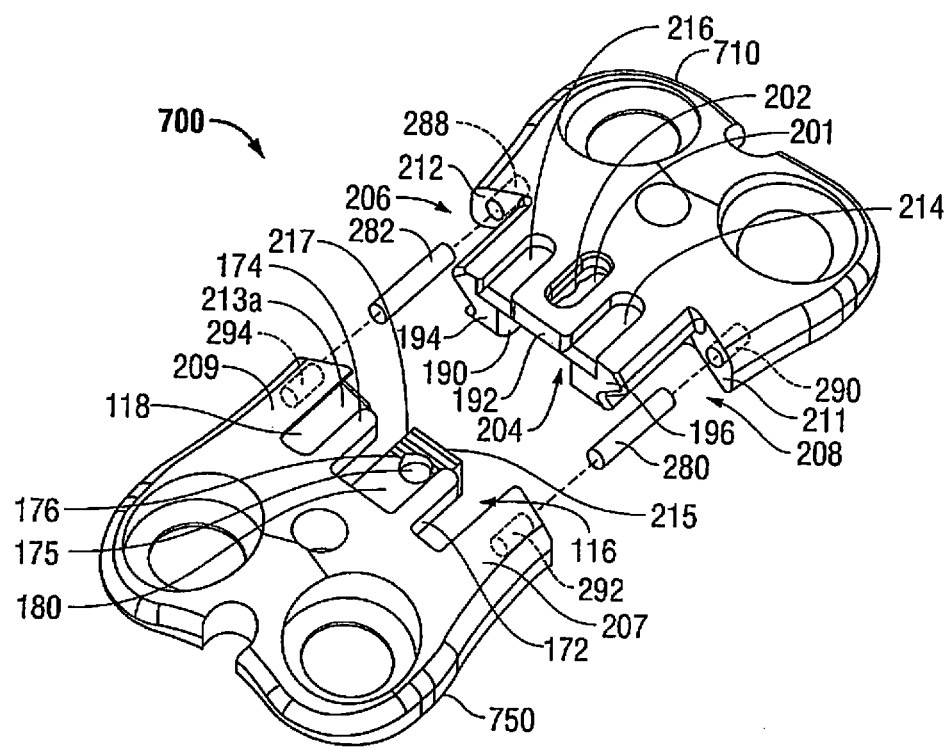
FIG. 16 is an exploded perspective view, with parts separated, of a further embodiment of the dynamic cervical plate in accordance with the present disclosure.

An alternate embodiment of the dynamic cervical plate is shown in FIG. 16 and is referred to as dynamic cervical plate 700. The first end section 710 includes a partition 192 that extends along the longitudinal axis thereof. The partition 192 is disposed between bar spaces 214, 216 for receiving bars 172, 174 and is mounted on a platform 190. A slide cavity 201 having elliptical outer boundaries extends transversely to the longitudinal axis disposed within the center of the partition 192 and through the platform 190 for receiving an interlocking pin 178. A plurality of ridges 202 extend downward from the underside of the slide cavity 201 about the perimeter thereof. A tongue space 204 is defined by the underside of the partition 192 and platform 190, the interior side walls of the bars 194, 196, and the ridges 202. Finger spaces 206, 208 are defined by the exterior sidewalls of the lower portion of the bars 194, 196, and the stop flanges 211, 212 abutting the body of the first end section 710. First and second support bar cavities 288, 290 are longitudinally disposed in the stop flanges 211, 212 and extend into the body of the first end section 710 for receiving first and second support bars 280, 282.

The second end section 750 includes first and second fingers 207, 209 and a tongue 215 that extend longitudinally. A receiving space 180 is defined between the interior walls of bars 172, 174. Additional receiving spaces 116, 118 are disposed between the interior walls of first and second fingers 207, 209 and the exterior walls of the bars 172, 174. The first and second fingers 207, 209 have grooves 213a, 213b disposed on the interior walls thereof. A first tooth 217 extends upwards from the distal end of the tongue 215. A second tooth 176 extends upwards from the distal end of the tongue 215 adjacent to the first tooth 217. A pin hole 175 extends transversely to the longitudinal axis through the center of the second tooth 176 and the tongue 215 at the distal end of the tongue 215 for receiving the interlocking pin 178. The tongue 215 is flexibly connected to the second end section 750 and is adapted to move above and below the plane defined by the lower surface of the second end section 750. Furthermore, first and second support bar cavities 292, 294 are longitudinally disposed in the distal end of the body of the second section 750 in spaced-apart relation relative to the longitudinal axis for receiving first and second support bars 280, 282. As described above, this embodiment also includes an orifice 106, a notch 102, and plurality of openings 105 with a lip 114 on each section for receiving a screw 10, 50.

Operation of the dynamic cervical plate 700 will now be described in detail. The second end section 750 is positioned to receive first and second support bars 280, 282 in first and second support bar cavities 292, 294. Alternatively, the first end section 710 is positioned to receive first and second support bars 280, 282 in first and second support bar cavities 292, 294. The support bars 280, 282 provide lateral support and minimize excess flexure between sections 710, 750. Second end section 750 is then connected to first end section 710 having the first and second support bars 280, 282 connected therebetween and disposed in first and second support bar cavities 292, 294 of second end section 750 and first and second support bar cavities 288, 290 of first end section 710. The pin 178 is inserted through the pin hole 175 and interconnects with the slide cavity 201. The tongue 215 engages the tongue space 204 and the teeth 217, 176 interconnect with the ridges 202. The pin 178 is inserted through the pin hole 175 and interconnects with the slide cavity 201. When the pin 178 interconnects the sections 710, 750, the pin 178 sets a maximum longitudinal length of the cervical plate 700. The plate 700, however, can get shorter, but not longer. The pin 178 is forwardly slidable in the slide cavity 201. However, as the teeth 176, 217 cantilever over the ridges 202 when the sections are brought in closer approximation, the teeth 176, 217 interlock with the ridges 202. Thus, rearward sliding and longitudinal expansion (lengthening) is minimized. In other words, the pin 178 defines a maximum length of the plate 700 while allowing for subsidence and inhibiting expansion or lengthening of the plate 700 once installed. The gap 462 is thus variable. As discussed above, screws 10, 50 are likewise compatible with this embodiment.

The dynamic cervical plate 700 comes preassembled in an open state. It is compressible to a completely collapsed state. The surgeon has the option to compress the plate 700 into closer approximation if it is open too much. The remaining gap 462 will subside over time in vivo. In some situations, the surgeon may wish to provide a maximum overall length of the cervical plate 700. In other situations, a minimum or intermediate position is more appropriate. Using a drill guide and screws, as are known in the art, the practitioner installs the dynamic cervical plate 700 across multiple vertebral bodies in the patient. The gap 462 is variable in response to relative movement between the first and second end sections 710, 750 with respect to each other. As the distance between the selected vertebral bodies decreases over time (i.e. subsidence), the first and second sections 710, 750 move relative to each other, thereby accommodating the subsidence without additional invasive procedures.

Figure 17:
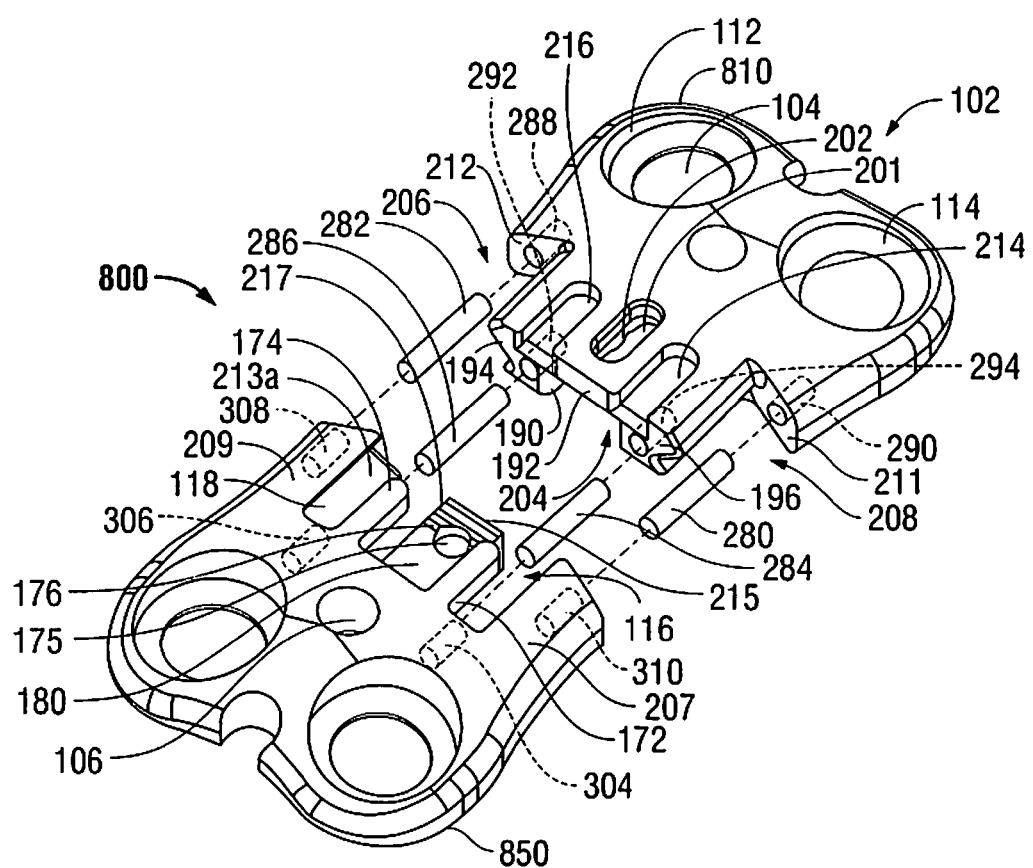
FIG. 17 is an exploded perspective view, with parts separated, of yet another embodiment of the dynamic cervical plate in accordance with the present disclosure.

An alternate embodiment of the dynamic cervical plate is shown in FIG. 17 and is referred to as dynamic cervical plate 800. The first end section 810 includes a partition 192 that extends along the longitudinal axis thereof. The partition 192 is disposed between bar spaces 214, 216 for receiving bars 172, 174 and is mounted on a platform 190. A slide cavity 201 having elliptical outer boundaries extends transversely to the longitudinal axis disposed within the center of the partition 192 and through the platform 190 for receiving an interlocking pin 178. A plurality of ridges 202 extend downward from the underside of the slide cavity 201 about the perimeter thereof. A tongue space 204 is defined by the underside of the partition 192 and platform 190, the interior side walls of the bars 194, 196, and the ridges 202. Finger spaces 206, 208 are defined by the exterior sidewalls of the bars 194, 196, and the stop flanges 211, 212 abutting the body of the first end section 810. First and second support bar cavities 288, 290 are longitudinally disposed in the stop flanges 211, 212 and extend into the body of the first end section 810 for receiving first and second support bars 280, 282. Third and fourth support bar cavities 292, 294 are longitudinally disposed in the lower portion of the bars 194, 196 for receiving third and fourth support bars 284, 286.

The second end section 850 includes first and second fingers 207, 209 and a tongue 215 that extend longitudinally. A receiving space 180 is defined between the interior walls of bars 172, 174. Additional receiving spaces 116, 118 are disposed between the interior walls of first and second fingers 207, 209 and the exterior walls of the bars 172, 174. The first and second fingers 207, 209 have grooves 213a, 213b disposed on the interior walls thereof. A first tooth 217 extends upwards from the distal end of the tongue 215. A second tooth 176 extends upwards from the distal end of the tongue 215 adjacent to the first tooth 217. A pin hole 175 extends transversely to the longitudinal axis through the center of the second tooth 176 and the tongue 215 at the distal end of the tongue 215 for receiving the interlocking pin 178. The tongue 215 is flexibly connected to the second end section 850 and is adapted to move above and below the plane defined by the lower surface of the second end section 850. First and second support bar cavities 308, 310 are longitudinally disposed in the distal end of the fingers 207, 209 for receiving first and second support bars 280, 282. Furthermore, third and fourth support bar cavities 304, 306 are longitudinally disposed in the distal end of the body of the second section 850 in spaced-apart relation relative to the longitudinal axis for receiving third and fourth support bars 284, 286. As described above, this embodiment also includes an orifice 106, a notch 102, and plurality of openings 105 with a lip 114 on each section for receiving a screw 10, 50.

Operation of dynamic cervical plate 800 will now be described in detail. The second end section 850 is positioned to receive first, second, third, and fourth support bars 280, 282, 284, 286 in first, second, third, and fourth support bar cavities 304, 306, 308, 310. Alternatively, the first end section 810 is positioned to receive first, second, third and fourth support bars 280, 282, 284, 286 in first, second, third and fourth support bar cavities 288, 290, 292, 294. The support bars 280, 282, 284, 286 provide lateral support and minimize excess flexure between sections 810, 850. Second end section 850 is connected to first end section 810 having the first, second, third and fourth support bars 280, 282, 284, 286 connected therebetween and disposed in their respective support bar cavities 304, 306, 308, 310 of second end section 850 and support bar cavities 288, 290, 292, 294 of first end section 810. The pin 178 is inserted through the pin hole 175 and interconnects with the slide cavity 201. When the pin 178 interconnects the sections 810, 850, the pin 178 sets a maximum longitudinal length of the cervical plate 800. The plate 800, however, can get shorter, but not longer. The pin 178 is forwardly slidable in the slide cavity 201. However, as the teeth 176, 217 cantilever over the ridges 202 when the sections are brought in closer approximation, the teeth 176, 217 interlock with the ridges 202. Thus, rearward sliding and longitudinal expansion (lengthening) is minimized. In other words, the pin 178 defines a maximum length of the plate 800 while allowing for subsidence and inhibiting expansion or lengthening of the plate 800 once installed. The gap between first and second end sections 810, 850 is thus variable. As discussed above, screws 10, 50 are likewise compatible with this embodiment.

The dynamic cervical plate 800 comes preassembled in an open state. It is compressible to a completely collapsed state. The surgeon has the option to compress the plate 800 into closer approximation if it is open too much. The practitioner adjusts the first end section 810 and the second end section 850 with respect to one another, thereby defining a gap therebetween. The size of the gap is dependant upon the patient and procedure being performed. In other words, in some situations, the surgeon may wish to provide a maximum overall length of the cervical plate 800. In other situations, a minimum or intermediate position may be more appropriate. The size of the gap may subside over time in vivo. Using a drill guide and screws, as are known in the art, the practitioner installs the dynamic cervical plate 800 across multiple vertebral bodies in the patient. The gap 462 is variable in response to relative movement between the first and second end sections 810, 850 with respect to each other. As the distance between the selected vertebral bodies decreases over time (i.e. subsidence), the first and second sections 810, 850 move relative to each other, thereby accommodating the subsidence without additional invasive procedures.

Figure 18:
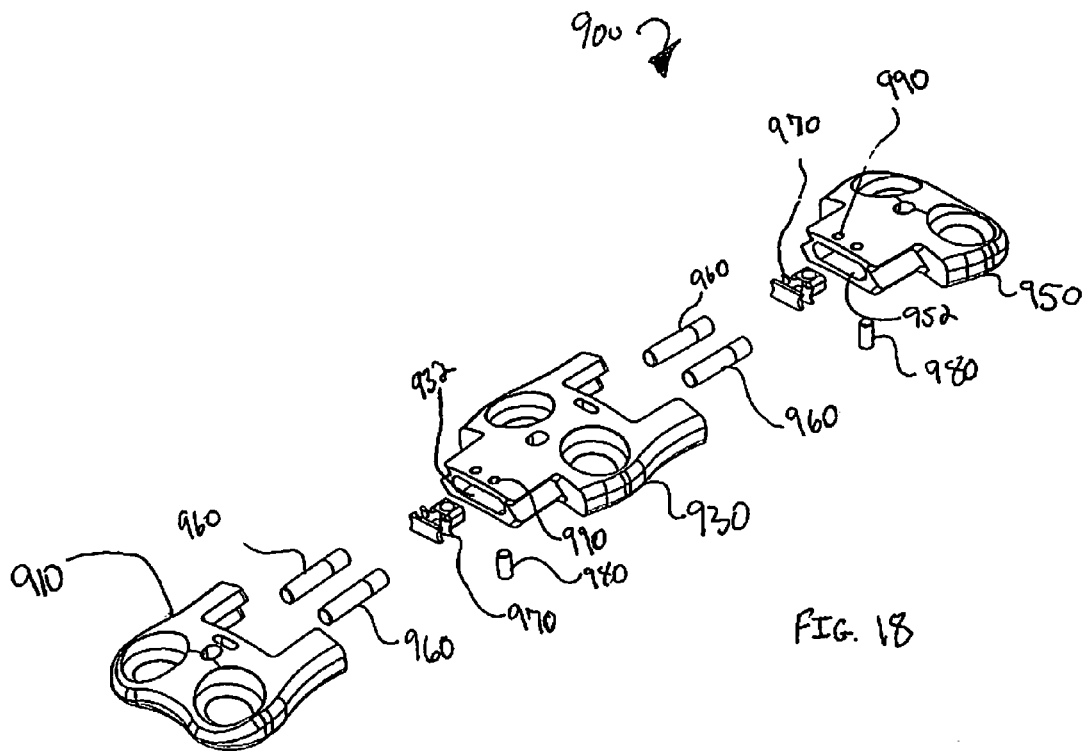
FIG. 18 is an exploded perspective view, with parts separated, of one embodiment of a dynamic cervical plate in accordance with the present disclosure.

An alternate embodiment of the dynamic cervical plate is shown in FIG. 18 and is referred to as dynamic cervical plate 900. In this embodiment, the first end section 910 is interconnected to the middle section 930 via two support bars 960 and a locking element 970. Similarly, the second end section 950 is interconnected to the middle section 930 by support bars 960 and a locking element 970. The support bars 960 are slidably positionable within support bar cavities (not shown) defined within the first section 910 and a first passage 932 defined within the middle section 930. Similarly, support bars 960 are slidably positionable within support bar cavities (not shown) defined within the middle section 930 and a second passage 952 defined within the second end section 950. Locking element 970 is positionable within the first passage 932 and mountable to the middle section 930 via pin 980. Similarly, locking element 970 is positionable within second passage 952 and is mountable to the second section 950 via pin 980. As described above with reference to FIGS. 1A and 1B, this embodiment also includes an orifice 106, a notch 102, and plurality of openings 104 with a lip 114 on each section for receiving a screw 10, 50 (FIGS. 6 and 7).

Figure 19:
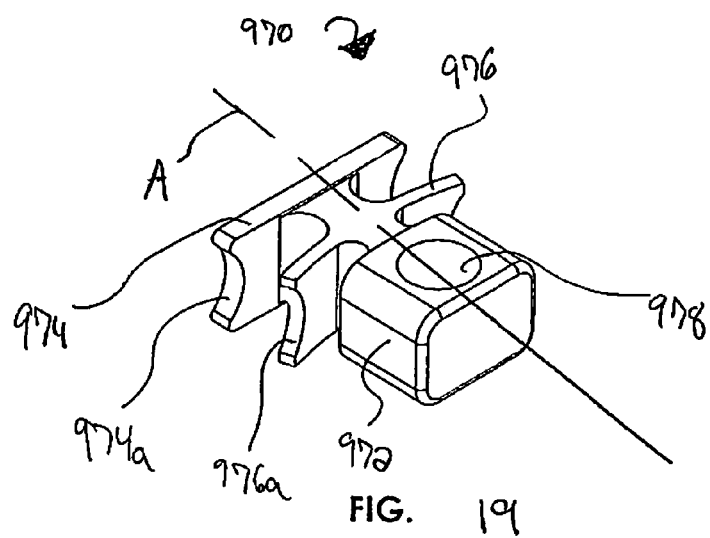
FIG. 19 is perspective view of one embodiment of a locking element in accordance with the present disclosure.

As best shown in FIG. 19, a locking element 970 includes a body 972, a first fin 974, and a second fin 976. The body 972 defines a pin opening 978 that is adapted to accommodate a pin 980 (FIG. 18) in order to mount the locking element 970 to the respective middle or second end section, 930, 950 (FIG. 18). As illustrated in FIG. 19, the first fin 974 and the second fin 976 are longitudinally adjacent relative to a longitudinal axis of the locking element. The first fin 974 defines a first profile 974a and the second fin 976 defines a second profile 976a. The first fin 974 is substantially perpendicular to a longitudinal axis "A" of the locking element 970 while the second fin 976 is disposed at an acute angle relative to the longitudinal axis "A." The second fin 976 may define an arc or a radius. In this manner, the first and second fins 974, 976 permit support bars 960 to slide along the profiles 974a, 976a as the dynamic cervical plate 900 compresses in response to subsidence while inhibiting longitudinal expansion. As the support bars 960 slide along the profiles 974a, 976a, the entire surface of (or portions thereof, e.g., a tangential relationship such as point or line contact) profile 976a may be in contact with the support bars 960 while the entire surface of (or portions thereof) the profile 974a may be offset from, i.e., not in contact with, the support bars 960. The first fin 974 is adapted to engage either first or second passages 932, 952 for substantially covering the respective first or second passage 932, 952. On the other hand, the second fin 976 is adapted to inhibit proximal movement and facilitate distal movement of the one or more support bars 960 as the dynamic cervical plate 900 moves in response to subsidence. In this manner, the second fin 976 enables movement of adjacent sections (i.e., section 910 is adjacent section 930 and section 930 is adjacent 950) toward each other (i.e., shortening) while preventing movement of the adjacent sections away from each other (i.e., lengthening). More particularly, the second fin 976 is biased in one direction such that the second fin, 976 may bend slightly to accommodate the insertion of the support bars 960. However, the fin 976 does not bend in the opposite direction in order to inhibit the removal of the support bars 960.

It is surgically preferred to maintain loading on the vertebral bodies so the healing process, or boney fusion can continue uninterrupted. Accordingly, the dynamic cervical plate 900 does not enable the sections 910, 930, 950 thereof to distract apart from one another. Should distraction be necessary, any suitable instrument (not shown) maybe inserted into one or more of the relief apertures 990 defined within sections 930, 950. The insertion of a suitable instrument within the relief apertures 990 releases the locking element 970 and allows adjacent sections (i.e., section 910 is adjacent section 930 and section 930 is adjacent section 950) to be separated by flexing the second fin 976. Specifically, the instrument bends the second fin 976 in the same direction that it normal bends, but the instruments bends the second fin 976 to a further degree in order to provide enough clearance between the respective support bar 960 and the second fin 976 so that the respective support bar 960 can slide past the second fin 976 relative to the locking element 970.

In embodiments, each section 910, 930, 950 may be made from commercially pure titanium or any other suitable material, the support bars 960 may be made from implant grade titanium alloy or any other suitable material, and the locking elements 970 may be made from cobalt chrome or any other suitable material. Some of the other suitable materials for the support bars 960 may include, but are not limited to, commercially pure titanium, titanium alloys, cobalt chrome alloys, PEEK, and the like materials. In embodiments, the support bars 960 may have a cross-section that may be circular or other alternate geometry such as square, triangular, I-beam, C-channel, or any other suitable non-circular or polygonal shape.

Operation of this embodiment of the dynamic cervical plate 900 will now be described in detail. First end section 910, second end section 950 and middle section 930 are all positioned relative to one another for receiving support bars 960, and locking elements 970. In embodiments, the support bars 960, may be manufactured integrally with respective sections 910, 930, 950. The support bars 960, and locking elements 970 are inserted into their respective sections 910, 930, 950. Each pin 980 is inserted through respective pin opening 978 of respective locking element 970 in order to mount the respective locking elements 970 to the respective sections. In this manner, the support bars 960 in combination with the locking elements 970 limit the maximum size of the plate 900 lengthwise such that the plate 900 can get shorter, but not longer. The support bars 960 may also provide lateral support and minimize excess flexure between sections 910, 930, 950. Once the support bars 960 and the locking elements 970 are positioned within the respective sections, the dynamic cervical plate 900 is enabled to maintain its integrity and position while also allowing for compression of the anatomy, constant loading of the bone graft, subsidence of the anatomy which may occur over time, and also allow for infinite adjustment along the length of the support bars 960.

The dynamic cervical plate 900 comes preassembled in an open state. It is compressible to a completely collapsed state. The surgeon has the option to compress the plate 900 into closer approximation if it is open too much. The plate 900 will subside over time in vivo. In some situations, the practitioner may adjust each of the sections 910, 930, 950 with respect to one another, depending upon the patient and procedure being performed. In some situations, the surgeon may wish to provide a maximum overall length of the cervical plate 900. In other situations, a minimum or intermediate position is more appropriate. Using a drill guide and screws, as are known in the art, the practitioner installs the dynamic cervical plate 900 across multiple vertebral bodies in the patient. As the distance between the selected vertebral bodies decreases over time (i.e. subsidence), the sections 910, 930, 950 move relative to each other, thereby accommodating the subsidence without additional invasive procedures. It is contemplated that additional middle sections 930 are included depending upon the particular procedure to be performed. As discussed above, screws 10, 50 are likewise compatible with this embodiment.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A spinal plate comprising:
a first section having a proximal end portion and a distal end portion, the first section defining a longitudinal axis that extends through the proximal and distal end portions, the first section including a longitudinally extending top surface, a longitudinally extending opposed bottom surface, and a first end face extending from the top surface to the bottom surface, the first section having a pair of fingers and a tongue extending from one end of the first section, each of the fingers including a groove along an interior surface thereof;
a space defined between each finger and the tongue;
a second section including a longitudinally extending top surface, a longitudinally extending opposed bottom surface, and a second end face extending from the top surface to the bottom surface, the second section having a pair of bars extending from one end of the second section, the pair of bars configured for being slidably received in the spaces between the tongue and the pair of fingers of the first section, such that when the first and second sections are slidably engaged with each other, the first and second sections are movable relative to each other;
a first support bar cavity defined in the first end face of the first section;
a second support bar cavity defined in the second end face of the second section so that the first and second support bar cavities face each other in opposed relation when the first and second sections are engaged; and
at least one support bar supported in the first and second support bar cavities between the first and second sections to provide lateral support to the first and second sections and minimize excessive flexure between the first and second sections.

2. The spinal plate according to claim 1, further comprising a third section having a second pair of bars extending from one end thereof and at least one second space for receiving a second tongue and a second pair of fingers disposed on the distal end of the second section, the second pair of fingers having at least one second groove along an interior surface thereof, wherein the second pair of bars slidably engages the at least one second groove and the second and third sections are slidably engaged along a longitudinal axis of the spinal plate.

3. The spinal plate according to claim 1, wherein the spinal plate defines a maximum length while being configured and dimensioned to allow for subsidence and inhibit longitudinal expansion.

4. The spinal plate according to claim 1, wherein at least one of the first section and the second section includes at least one tooth, wherein the at least one tooth is configured and dimensioned to engage at least one lip disposed on the other section.

5. The spinal plate according to claim 4, wherein engagement of the at least one tooth and the at least one lip defines a maximum length of the spinal plate.

6. The spinal plate according to claim 1, wherein at least one of the first section and the second section includes at least one tooth, wherein the at least one tooth is configured and dimensioned to engage at least one ridge disposed on the other section.

7. The spinal plate according to claim 6, wherein engagement of the at least one tooth and the at least one ridge defines a maximum length of the spinal plate.

8. The spinal plate according to claim 1, wherein each support bar cavity includes an open terminal end for the reception of an end of the support bar and a closed terminal end that limits axial movement of the end of the support bar along an axis extending through the open and closed terminal ends, the axis being parallel to a longitudinal axis extending between the first and second sections.

9. The spinal plate according to claim 1, further comprising at least one pin interconnecting at the first and second sections, the pin at least partially disposed in a pin hole defined within one of the first section and the second section, the pin at least partially disposed in a slide cavity defined within the other section.

10. The spinal plate according to claim 1, wherein at least one section includes at least one opening configured and dimensioned to receive a fastener.

11. The spinal plate according to claim 10, wherein the at least one opening has an annular lip disposed therein.

12. The spinal plate according to claim 1, wherein at least one of the first section and the second section is configured and dimensioned to receive a drill guide.

13. The spinal plate of claim 1, wherein the at least one support bar is cylindrical.

14. A spinal plate system comprising:
a body having a proximal end portion and a distal end portion, the body defining a longitudinal axis that extends through the first and second end portions, the body including first and second sections, the first and second sections being slidably engagable with one another such that each section is movable relative to the other section along the longitudinal axis, each section defining a top surface and an opposed bottom surface, the top and bottom surfaces extending along the longitudinal axis, and an end face that extends from the top surface to the bottom surface, each respective end face defining a support bar cavity, the support bar cavities extending along the longitudinal axis, at least one of the first and second sections being adapted to engage a screw for mounting one of the first and second sections to a vertebral body, the screw being formed of a first material and one of the first and second sections being formed of a second material, one of the first and second materials being softer than the other of the first and second materials such that when the screw is engaged with one of the first and second sections, the screw is inhibited from disengaging;
a support bar mounted within the support bar cavities of the first and second sections to provide lateral support to the first and second sections and minimize excessive flexure between the first and second sections, the support bar extending along the longitudinal axis; and
a locking element that enables the first and second sections to move toward each other but inhibits the first and second sections from moving away from each other.

15. The spinal plate system according to claim 14, further including a third section slidably engageable with at least one of the first and second sections and operably coupled to at least one of the first and second sections with a second support bar and a second lockingelement.

16. The spinal plate system according to claim 14, wherein at least one of the first and second sections includes a relief aperture that permits adjustment of the first and second sections relative to one another.

17. The spinal plate system of claim 14, wherein the support bar is cylindrical.

18. The spinal plate system of claim 14, wherein a portion of the support bar is positioned in a gap between the first and second sections.

* * * * *